United States Patent [19]

Torizuka et al.

[11] Patent Number: 5,028,604

[45] Date of Patent: Jul. 2, 1991

[54] CONDENSED BENZENE DERIVATIVE

[75] Inventors: Motoki Torizuka, Saitama; Tomoji Aotsuka, Yaizu; Mitsuo Soeda; Kuniyoshi Ogura, both of Konan; Yoshiaki Tanaka, Konan; Hisayoshi Kato, Konan; Naoki Nakata, Konan; Naoyoshi Miura, Konan; Hikari Morita, Konan, all of Japan

[73] Assignee: Zeria Pharmaceutical Co., Ltd., Tokyo, Japan

[21] Appl. No.: 444,702

[22] Filed: Dec. 1, 1989

[30] Foreign Application Priority Data

Dec. 8, 1988 [JP] Japan .................................. 63-308878
Oct. 6, 1989 [JP] Japan .................................. 1-260070

[51] Int. Cl.$^5$ .................. C07D 417/06; C07D 403/06; A61K 31/425; A61K 31/40
[52] U.S. Cl. .................. 514/227.8; 514/326; 514/365; 514/423; 544/60; 546/208; 546/209; 548/200; 548/201; 548/530; 548/532; 548/539
[58] Field of Search .............. 548/200, 201, 530, 532, 548/539; 514/227.8, 326, 365, 423; 544/60; 546/208, 209

[56] References Cited

U.S. PATENT DOCUMENTS 4,857,537 8/1989 Taka ................................... 514/365

FOREIGN PATENT DOCUMENTS 0232849 8/1987 European Pat. Off. .
0268281 5/1988 European Pat. Off. .
0321956 6/1989 European Pat. Off. .
1230578 9/1989 Japan .................................. 548/200

OTHER PUBLICATIONS

Chemical Abstracts, No. 92, No. 17, Apr. 28, 1990, p. 564, Abstract No. 146492h, Columbus, Ohio, U.S.; & JP-A-79 138 551 (Sumittomo Chemical Co., Ltd.), 27-10-1979.
Journal of the Chemical Society, Chemical Communications, 1981, pp. 1100–1101, London, GB; R. N. Warrener et al.: "Preparation of (−)-(7R)-7-acetyl-7-hydroxy-4,4-dimethoxy-5,6,7,8-tetrahydronapthalen-1 (4H)-one, a Chiral AB-Synthon for Anthracycline Synthesis", p. 1100, Compounds 7,8.
J. Biochem., vol. 104, No. 4, Oct. 1988, pp. 580–586, Tokyo, JP; D. Tsuru et al.: "Thiazolidine Derivatives as Potent Inhibitors Specific for Prolyl Endopeptidase".

Primary Examiner—Robert Gerstl
Attorney, Agent, or Firm—Oblon, Spivak, McClelland, Maier & Neustadt

[57] ABSTRACT

Novel condensed benzene derivatives having prolyl endopeptidase inhibitory, anti-hypoxic, and anti-amnesic activities are disclosed. The compounds are represented by the following (I),

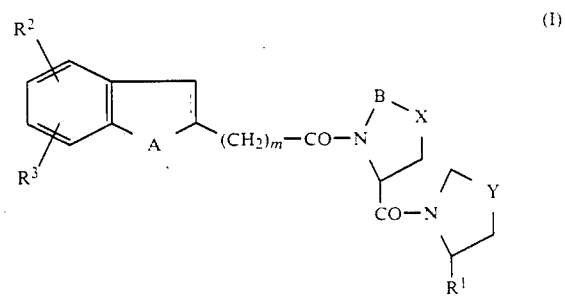

wherein A represents a methylene, ethylene, or propylene group, B represents a methylene or ethylene group, m denotes an integer of 0–5, X and Y, which may be same or different, individually represent a methylene group or sulfur atom, $R^1$ represents a hydrogen atom, a carboxyl, lower alkyloxycarbonyl, hydroxymethyl, or formyl group, $R^2$ represents a hydrogen atom, a halogen atom, a lower alkyl, lower alkoxy, nitro, or amino group, $R^3$ represents a hydrogen atom or a lower alkyl group, and the dotted line may optionally be present. They are useful as a medicine for treating or preventing cerebral circulation disorder, cerebral metabolism disorder, or memory disturbance.

5 Claims, No Drawings

CONDENSED BENZENE DERIVATIVE

BACKGROUND OF THE INVENTION

1. Field of the Invention

This invention relates to condensed benzene derivatives, a medicine for treating or preventing cerebral circulation disorder, cerebral metabolism disorder, and memory disturbance comprising the same, and intermediates for preparing the same.

2. Description of the Background Art

Senile dementia caused by such cerebral disorders as cerebrovascular disorder, cerebral circulation disorder, cerebral metabolism disorder, and memory disturbance has become a social problem in the society with prolonged lifespan. Development of medicines useful for treating or preventing these diseases are thus desired.

A recent clinical report [M. F. Mazurek et al., Neurology, 36, 1133 (1986)] revealed a remarkable decrease of peptides participating in memory or neurotransmission in brains of senile dementia patients.

Prolyl endopeptidase inhibitors are known as exhibiting anti-amnesic activity, since prolyl endopeptidase hydrolyzes and inactivates neuropeptides including proline in brains such as vasopressin [European Patent Publication No. 232849, Folia Pharmacologica Japonica, 89, 323 (1987), and id., 89, 243 (1987)].

Drugs improving cerebral circulation, cerebral vasodilators, cerebral metabolism accelerators, and the like are clinically used as medicines for treating cerebrovascular disorders. These medicines, however, exhibit only insufficient improvement in neurological symptoms or inability of daily life in the patients, even though they are recognized to improve subjective symptoms. Therefore, development of a medicine possessing both cerebral metabolism improving effects and anti-amnesic effects based on prolyl endopeptidase inhibitory activity has been desired.

The present inventors have undertaken extensive studies on various compounds in order to obtain a novel medicine for treating or preventing cerebral circulation disorder, cerebral metabolism disorder, and memory disturbance. As a result, the present inventors found that a condensed benzene derivative represented by the following formula (I) exhibited both prolyl endopeptidase inhibitory activity, anti-hypoxic activity and anti-amnesic and cerebral circulation/metabolism improving activity at the same time. Such a finding has led to the completion of the present invention.

SUMMARY OF THE INVENTION

Accordingly, an object of this invention is to provide a condensed benzene derivative represented by the following (I),

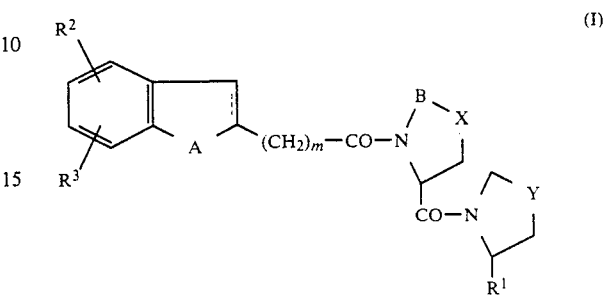

wherein A represents a methylene, ethylene, or propylene group, B represents a methylene or ethylene group, m denotes an integer of 0-5, X and Y which may be same or different represent a methylene group or a sulfur atom, $R^1$ represents a hydrogen atom, a carboxyl, lower alkyloxycarbonyl, hydroxymethyl, or formyl group, $R^2$ represents a hydrogen atom, a halogen atom, a lower alkyl, lower alkoxy, nitro, or amino group, $R^3$ represents a hydrogen atom or a lower alkyl group, and the dotted line may optionally be present; a medicine for treating or preventing cerebral circulation disorder, cerebral metabolism disorder, and memory disturbance comprising the condensed benzene derivative; and an intermediate for preparing the condensed benzene derivative.

DETAILED DESCRIPTION OF THE INVENTION AND PREFERRED EMBODIMENTS

A lower alkyl group in this invention is defined as linear or branched alkyl group having 1-6 carbon atoms. Specific examples of the lower alkyl groups are methyl, ethyl, propyl, isopropyl, butyl, sec-butyl, isobutyl, t-butyl, and the like. A lower alkoxy group is defined as linear or branched alkoxy group having 1-6 carbon atoms. Specific examples are methoxy, ethoxy, propoxy, isopropoxy, butoxy, and the like.

The compound of the present invention can be prepared, for example, according to the following reaction formula.

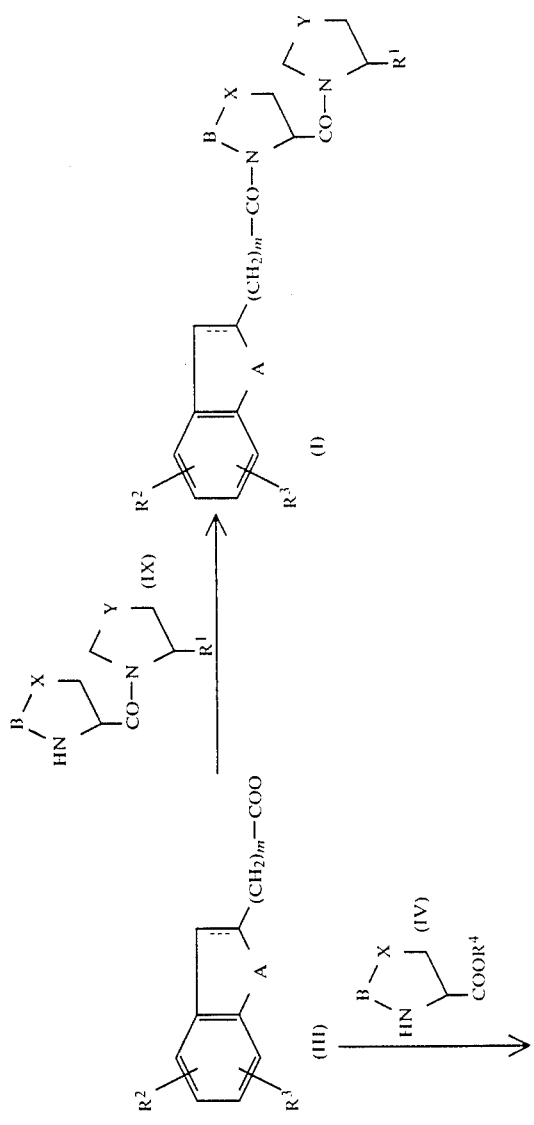
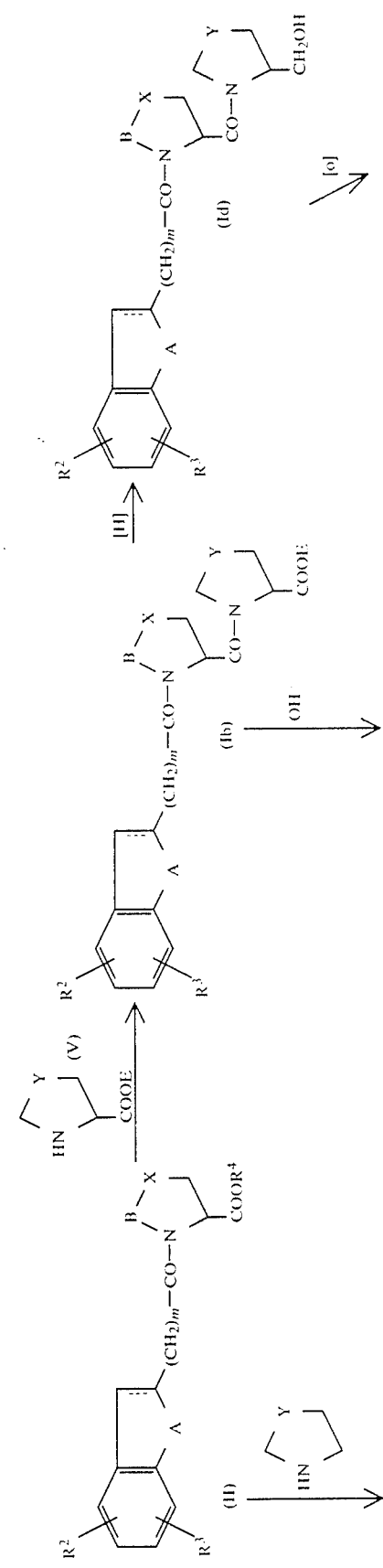

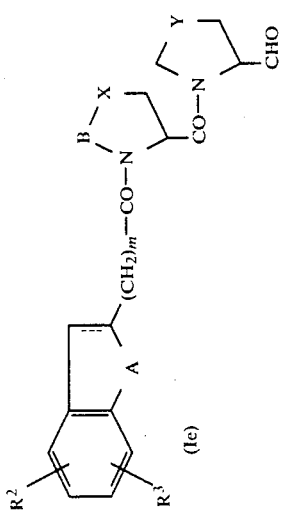
(Ie)
-continued
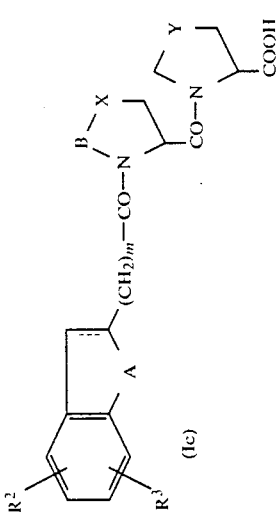
(Ic)
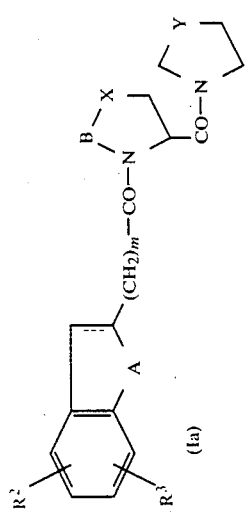
(Ia)

In the above reaction formula, D in compound (III) represents a halogen atom, a lower alkoxy group, or a hydroxyl group, $R^4$ in compounds (II) and (IV) represents a hydrogen atom or a lower alkyl group, E in compound (Ib) and (V) represents a lower alkyl group, and $R^1$, $R^2$, $R^3$, X, Y, A, B, and m in several compounds have the same meanings defined for formula (I).

Each step of the reactions is now described.

An acid halide, ester, or carboxylic acid (III) is reacted with a cyclic amino acid compound (IV) in the presence or absence of a base to produce an N-substituted cyclic amino acid derivative (II). The compound (III), when D in formula (III) is a halogen atom or a lower alkoxy group, can be condensed with compound (IV). It is desirable to use a carbodiimide as a condensing agent when D in formula (III) is a hydroxyl group. Alkali metal hydroxides or carbonates, trialkyl amines, aromatic amines. A desirable base is sodium hydroxide, potassium hydroxide, or the like. As carbodiimides, 1-ethyl-3-(3-dimethylaminopropyl)carbodiimide (WSC) or its hydrochloride, N,N'-dicyclohexylcarbodiimide (DCC), or the like are given. The reaction temperature is −20° to 200° C. Any solvent which does not involve in the reaction may be used.

Following compounds are given as typical examples of an N-substituted cyclic amino acid derivatives (II) thus prepared, which are intermediates of the compound of the present invention.

1-(2-indanylacetyl)-L-proline methyl ester,
1-[3-(indan-2-yl)propionyl]-D-proline ethyl ester,
1-(2-indanylacetyl)-L-proline,
3-(2-indanylacetyl)-L-thioproline ethyl ester,
3-[4-(indan-2-yl)butanoyl]-L-thioproline propyl ester,
3-(2-indanylacetyl)-L-thioproline,
Ethyl 1-(2-indanylacetyl)-DL-piperidin-2-ylcarboxylate,
Ethyl 1-(2-indanylacetyl)-L-piperidin-2-ylcarboxylate,
Butyl 1-[5-(indan-2-yl)pentanoyl]-L-piperidin-2-ylcarboxylate,
1-(2-indanylacetyl)-DL-piperidin-2-ylcarboxylic acid,
1-(2-indanylacetyl}-D-piperidin-2-ylcarboxylic acid,
1-(2-indanylacetyl)-L-piperidin-2-ylcarboxylic acid,
Methyl 4-(2-indanylacetyl)-DL-1,4-thiazan-3-ylcarboxylate,
Ethyl 4-(2-indanylacetyl)-DL-1,4-thiazan-3-ylcarboxylate,
Ethyl 4-(2-indanylacetyl)-L-1,4-thiazan-3-ylcarboxylate,
4-(2-indanylacetyl)-DL-1,4-thiazan-3-ylcarboxylic acid,
4-(2-indanylacetyl)-D-1,4-thiazan-3-ylcarboxylic acid,
4-[4-(indan-2-yl)butanoyl]-L-1,4-thiazan-3-ylcarboxylic acid,
4-(2-indanylcarbonyl)-DL-1,4-thiazan-3-ylcarboxylic acid,
1-(1,2,3,4-tetrahydronaphthalen-2-ylcarbonyl)-L-proline methyl ester,
1-(1,2,3,4-tetrahydronaphthalen-2-ylacetyl)-D-proline ethyl ester,
1-(1,2,3,4-tetrahydronaphthalen-2-ylcarbonyl)-L-proline,
1-(1,2,3,4-tetrahydronaphthalen-2-ylacetyl)-L-proline,
3-(1,2,3,4-tetrahydronaphthalen-2-ylcarbonyl)-L-thioproline ethyl ester,
3-(1,2,3,4-tetrahydronaphthalen-2-ylcarbonyl)-L-thioproline,
3-[3-(1,2,3,4-tetrahydronaphthalen-2yl)propionyl]-DL-thioproline,
1-(1,2,3,4-tetrahydronaphthalen-2-ylacetyl)-L-proline methyl ester,
1-(1,2,3,4-tetrahydronaphthalen-2-ylacetyl)-D-proline methyl ester,
1-(1,2,3,4-tetrahydronaphthalen-2-ylacetyl)-D-proline,
3-(1,2,3,4-tetrahydronaphthalen-2-ylacetyl)-L-thioproline ethyl ester,
3-(1,2,3,4-tetrahydronaphthalen-2-ylacetyl)-D-thioproline ethyl ester,
3-(1,2,3,4-tetrahydronaphthalen-2-ylacetyl)-L-thioproline,
3-(1,2,3,4-tetrahydronaphthalen-2-ylacetyl)-D-thioproline,
1-(1,2,3,4-tetrahydronaphthalen-2-ylcarbonyl)-L-piperidine-2-ylcarboxylic acid,
1-(1,2,3,4-tetrahydronaphthalen-2-ylcarbonyl)-D-piperidine-2-ylcarboxylic acid,
1-[6-(1,2,3,4-tetrahydronaphthalen-2-yl)hexanoyl]-L-piperidin-2-ylcarboxylic acid,
Methyl 4-(1,2,3,4-tetrahydronaphthalen-2-ylcarbonyl)-DL-1,4-thiazan-3-ylcarboxylate,
4-(1,2,3,4-tetrahydronaphthalen-2-ylcarbonyl)-DL-1,4-thiazan-3-ylcarboxylic acid,
4-(1,2,3,4-tetrahydronaphthalen-2-ylcarbonyl)-L-1,4-thiazan-3-ylcarboxylic acid,
4-(1,2,3,4-tetrahydronaphthalen-2-ylcarbonyl)-D-1,4-thiazan-3-ylcarboxylic acid,
4-[4-(1,2,3,4-tetrahydronaphthalen-2-yl)butanoyl]-L-1,4-thiazan-3-ylcarboxylic acid,
1-(2-indenylacetyl)-L-proline methyl ester,
1-(2-indenylacetyl)-L-proline,
1-(2-indenylacetyl)-D-proline,
3-(2-indenylacetyl)-L-thioproline ethyl ester,
3-(2-indenylacetyl)-L-thioproline propyl ester,
3-(2-indenylacetyl)-L-thioproline,
Ethyl 1-(2-indenylacetyl)-DL-piperidin-2-ylcarboxylate,
Ethyl 1-(2-indenylacetyl)-L-piperidin-2-ylcarboxylate,
Methyl 1-[5-(inden-2-yl)pentanoyl]-L-piperidin-2-ylcarboxylate,
1-(2-indenylacetyl)-DL-piperidin-2-ylcarboxylic acid,
1-(2-indenylacetyl)-D-piperidin-2-ylcarboxylic acid,
1-(2-indenylacetyl)-L-piperidin-2-ylcarboxylic acid,
Ethyl 4-(2-indenylacetyl)-DL-1,4-thiazan-3-ylcarboxylate,
Butyl 4-(2-indenylacetyl)-L-1,4-thiazan-3-ylcarboxylate,
Methyl 4-[4-(inden-2-yl)butanoyl]-L-1,4-thiazan-3-ylcarboxylate,
4-(2-indenylacetyl)-DL-1,4-thiazan-3ylcarboxylic acid,
4-(2-indenylacetyl)-L-1,4-thiazan-3-ylcarboxylic acid,
4-(2-indenylacetyl)-D-1,4-thiazan-3-ylcarboxylic acid,
4-(2-indenylcarbonyl)-DL-1,4-thiazan-3-ylcarboxylic acid,
4-(2-indenylcarbonyl)-L-1,4-thiazan-3-ylcarboxylic acid,
4-(2-indenylcarbonyl)-D-1,4-thiazan-3-ylcarboxylic acid,
1-(2-indanylcarbonyl)-L-proline,
1-[5-(indan-2-yl)pentanoyl]-L-proline,
1-[6-(indan-2-yl)hexanoyl]-L-proline,
1-(5-methoxy-6-methylindan-2-ylacetyl)-L-proline,
1-(5-methoxyinden-2-ylacetyl)-L-proline,
1-[3-(inden-2-yl)propionyl]-L-proline,
1-(5-aminoinden-2-ylacetyl)-L-proline,
1-(6-methoxy-1,2,3,4-tetrahydronaphthalen-2-ylacetyl)-L-proline, 1-(8-methyl-6-nitro-1,2,3,4-tetrahydronaphthalen-2-ylacetyl)-L-proline,
1-(2,3,4,5-tetrahydro-1H-benzocyclohepten-2-ylacetyl)-L-proline,
1-[3-(indan-2-yl)propionyl]-D-proline,
3-(5-aminoindan-2-ylacetyl)-L-thioproline,
3-(5-nitroindan-2-ylacetyl)-L-thioproline,
3-(5-chloroindan-2-ylacetyl)-L-thioproline,
3-[3-(indan-2-yl)propionyl]-L-thioproline,
3-[4-(indan-2-yl)butanoyl]-L-thioproline,
3-(2-indanylacetyl)-D-thioproline,
3-[3-(5-methoxyinden-2-yl)propionyl]-L-thioproline,
3-[3-(5-aminoinden-2-yl)propionyl]-L-thioproline,
3-(6-methoxy-1,2,3,4-tetrahydronaphthalen-2-ylacetyl)-L-thioproline,
3-(6-amino-1,2,3,4-tetrahydronaphthalen-2-ylacetyl)-L-thioproline,
3-[3-(1,2,3,4-tetrahydronaphthalen2yl)propionyl]-L-thioproline,
3-(5,7-dimethyl-1,2,3,4-tetrahydronaphthalen-2-ylacetyl)-L-thioproline,
3-(2,3,4,5-tetrahydro-1H-benzocyclohepten-2-ylacetyl)-L-thioproline,
3-(5-chloro-7-methyl-1,2,3,4-tetrahydronaphthalen-2-ylacetyl)-L-thioproline,
3-(2-indanylacetyl)-DL-thioproline,
1-(1,2,3,4-tetrahydronaphthalen-2-ylacetyl)-DL-piperidine-2-ylcarboxylic acid,
1-[3-(2,3,4,5-tetrahydro-1H-benzocyclohepten-2-yl)propionyl]-DL-piperidin-2-ylcarboxylic acid,
4-(1,2,3,4-tetrahydronaphthalen-2-ylacetyl)-DL-1,4-thiazan-3-ylcarboxylic acid,
4-[5-(inden-2-yl)pentanoyl]-L-1,4-thiazan-3-ylcarboxylic acid,
4-[6-(1,2,3,4-tetrahydronaphthalen-2-yl)hexanoyl]-L-1,4-thiazan-3-ylcarboxylic acid,
1-[(S)-(−)-1,2,3,4-tetrahydronaphthalen-2-ylacetyl]-L-proline,
1-[(R)-(+)-1,2,3,4-tetrahydronaphthalen-2-ylacetyl]-L-proline,
3-[(S)-(−)-1,2,3,4-tetrahydronaphthalen-2-ylacetyl]-L-thioproline,
3-[(R)-(+)-1,2,3,4-tetrahydronaphthalen-2-ylacetyl]-L-thioproline,
3-[(S)-(−)-1,2,3,4-tetrahydronaphthalen-2-ylacetyl]-D-thioproline,
4-(2,3,4,5-tetrahydro-1H-benzocyclohepten-2-ylacetyl)-L-1,4-thiazan-3-ylcarboxylic acid,
3-[3-(5-methylindan-2-yl)propionyl]-L-thioproline ethyl ester,
3-(6-methoxy-5-methylindan-2-ylacetyl)-L-thioproline ethyl ester,
3-(6-methoxy-1,2,3,4-tetrahydronaphthalene-2-ylacetyl)-L-thioproline ethyl ester,
3-(6-amino-1,2,3,4-tetrahydronaphthalen-2-ylacetyl)-L-thioproline ethyl ester,
3-(5,7-dimethyl-1,2,3,4-tetrahydronaphthalen-2-ylacetyl)-L-thioproline ethyl ester,
1-(5-methoxyindan-2-ylacetyl)-L-proline methyl ester,
1-(5-chloroindan-2-ylacetyl)-L-proline methyl ester,
1-(5-amino-6-methylindan-2-ylacetyl)-L-proline methyl ester,
1-(6-methoxy-1,2,3,4-tetrahydronaphthalen-2-ylacetyl)-L-proline methyl ester,
1-(6-methyl-7-nitro-1,2,3,4-tetrahydronaphthalene-2-ylacetyl)-L-proline methyl ester,
1-[5-(inden-2-yl)pentanoyl]-D-proline ethyl ester,
Ethyl 1-(1,2,3,4-tetrahydronaphthalen-2-ylacetyl)-L-piperidin-2-ylcarboxylate,
Butyl 1-[6-(7-chloro-2,3,4,5-tetrahydro-1H-benzocycloheptan-2-yl)hexanoyl]-L-piperidin-2-ylcarboxylate,
Ethyl 1-(7-amino-6-methyl-1,2,3,4-tetrahydronaphthalene-2-ylcarbonyl)-DL-piperidin-2-ylcarboxylate,
Methyl 1-[5-(indan-2-yl)pentanoyl]-L-piperidin-2-ylcarboxylate,
Ethyl 4-[5-(5-methoxy-6-methylinden-2-yl)pentanoyl]-L-1,4-thiazan-3-ylcarboxylate,
Ethyl 4-[4-(7-amino-2,3,4,5-tetrahydro-1H-benzocycloheptene-2-yl)butanoyl]-DL-1,4-thiazan-3-ylcarboxylate,
Butyl 4-[5-(7-chloro-2,3,4,5-tetrahydro-1H-benzocyclohepten-2-yl)pentanoyl]-L-1,4-thiazan-3-ylcarboxylate,
1-[(S)-(−)-1,2,3,4-tetrahydronaphthalen-2-ylacetyl]-L-proline methyl ester,
1-[(R)-(+)-1,2,3,4-tetrahydronaphthalen-2-ylacetyl]-L-proline methyl ester,
3-[(S)-(−)-1,2,3,4-tetrahydronaphthalen-2-ylacetyl]-L-thioproline ethyl ester,
3-[(R)-(+)-1,2,3,4-tetrahydronaphthalen-2-ylacetyl]-L-thioproline ethyl ester,
3-[(S)-(−)-1,2,3,4-tetrahydronaphthalen-2-ylacetyl]-D-thioproline ethyl ester A condensation reaction of an N-substituted cyclic amino acid derivative (II) and thiazolidine or pyrrolidine produces the compound (Ia), which is a compound having a hydrogen atom for $R^1$ in formula (I).

When the condensation reaction of an N-substituted cyclic amino acid derivative (II) and a proline alkyl ester or thioproline alkyl ester of formula (V) is carried out, the compound (Ib) is produced, which is a compound having a lower alkyl ester group for $R^1$ in formula (I).

Here, a commonly used condensing agent can be used in the condensation reactions. Preferable condensing agents are carbodiimides such as WSC, WSC.HCl, DCC, or the like. Any solvents which are inert to the reaction can be used. Examples of preferable solvents are methylene chloride, chloroform, tetrahydrofuran, dioxane, and the like. The reaction temperature of −20° to 80° C., preferably of 0° to 40° C., is applied.

Other condensation methods which are commonly employed, for example, the acid chloride method, the mixed anhydride method, or the like [Izumiya et al.; PEPTIDE GOUSEI NO KISO TO JIKKEN; Maruzen Publishing Co. (1985)] may also be used.

The compound (1c), which is a compound having a carboxyl group for $R^1$ in formula (I), can be prepared by hydrolyzing a compound of formula (1b).

Further, the compound (1d), which is a compound having a hydroxymethyl group for $R^1$ in formula (I), can be prepared by reducing a compound of formula (1b). A borohydride such as sodium borohydride, lithium borohydride, zinc borohydride, potassium borohydride, or the like is preferable as a reducing agent. As a solvent, an alcohol such as methanol, ethanol, propanol, isopropanol, butanol, t-butanol, or the like, or an ether such as tetrahydrofuran, dioxane, or the like is preferably used.

Furthermore, the compound (1e), which is a compound having a formyl group for $R^1$ in formula (I), can be prepared by oxidizing a compound of formula (1d). Preferable oxidizing agents are dimethyl sulfoxide, chromium trioxide-pyridine complex, t-butyl chloro formate, silver oxide, manganese dioxide, and the like. The reaction is carried out in the presence or absence of an inert organic solvent such as methylene chloride, chloroform, benzene, or the like, at room temperature or with cooling. When dimethyl sulfoxide is used as a oxidizing agent, it is desirable to use an activation agent such as sulfur trioxide-pyridine complex, oxalyl chloride, dicyclohexyl carbodiimide, or the like.

In the process of the present invention, a cyclic amino acid compound (IV) of DL-, D, or L-configuration produces the corresponding compound (I and N-substituted amino acid derivative (II) having DL-, D, or L-configuration. There are 1-3 assymetric carbon atoms in compound (I) of the present invention. The configulation of each assymetric carbon atom can be either S or R. The present invention also includes mixtures S- and R-configuration isomers.

A compound of formula (I) can also be prepared by the condensation reaction of a compound of the formula (III) and a compound of the formula (IX). The method of the condensation is the same as the above-mentioned condensation process for producing compounds of formula (I).

The compound of the formula (IX) can be prepared according to the following reaction formula,

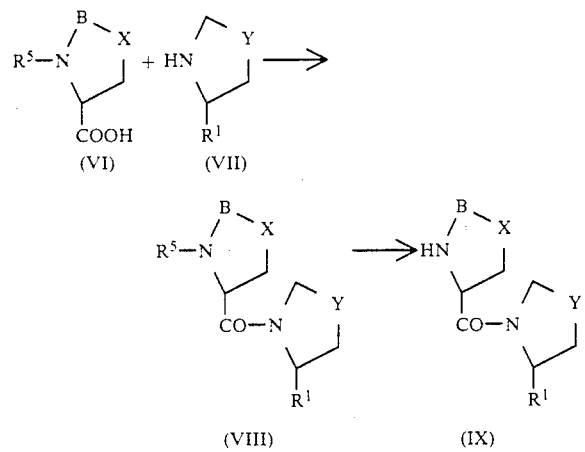

wherein $R^5$ is a protective group for an amino acid, B, X, Y, and $R^1$, have the same meanings as defined previously.

According to the above reaction formula, a cyclic amino acid compound (VI) and a cyclic amine (VII) is reacted to produce a compound (VIII). A compound (IX) is prepared by removing the protective group R5 from the compound (VIII).

Enumerated below are a number of compounds (I) of the present invention which are prepraed by the method discussed above.

1-[1-(2-indanylacetyl)-L-prolyl]pyrrolidine,
1-[1-(2-indanylacetyl)-D-prolyl]pyrrolidine,
3-[1-(2-indanylacetyl)-DL-prolyl]thiazolidine,
3-[1-(2-indanylacetyl)-L-prolyl]thiazolidine,
1-[1-(2-indanylacetyl)-L-prolyl]-L-proline methyl ester,
1-[1-(2-indanylacetyl)-L-prolyl]-L-prolinol,
1-[1-(2-indanylacetyl)-L-prolyl]-L-proline,
1-[1-(2-indanylacetyl)-L-prolyl]-L-prolinal,
3-[1-(2-indanylacetyl)-L-prolyl]-L-thioprolinal,
1-{1-[3-indan-2-yl)propionyl]-L-prolyl}pyrrolidine,
1-[1-(2-indanylcarbonyl)-L-prolyl]pyrrolidine,
1-[3-(2-indanylacetyl)-L-thioprolyl]pyrrolidine,
1-[3-(2-indanylacetyl)-D-thioprolyl]pyrrolidine,
3-[3-(2-indanylacetyl)-DL-thioprolyl]thiazolidine,
3-[3-(2-indanylacetyl)-L-thioprolyl]thiazolidine,
1-[3-(2-indanylacetyl)-L-thioprolyl]-L-prolinal,
3-[3-(2-indanylacetyl)-L-thioprolyl]-L-thioproline methyl ester,
3-[3-(2-indanylacetyl)-L-thioprolyl]-L-thioprolinol,
3-[3-(2-indanylacetyl)-L-thioprolyl]-L-thioproline,
3-[3-(2-indanylacetyl)-L-thioprolyl]-L-thioprolinal,
3-{3-[4-(indan-2-yl)butanoyl]-L-thioprolyl}thiazolidine,
1-[1-(2-indanylacetyl)-DL-piperidin-2-ylcarbonyl]pyrrolidine,
1-[1-(2-indanylacetyl)-L-piperidin-2-ylcarbonyl]pyrrolidine,
1-[1-(2-indanylacetyl)-D-piperidin-2-ylcarbonyl]pyrrolidine,
1-[1-(2-indanylacetyl)-L-piperidin-2-ylcarbonyl]-L-proline methyl ester,
1-[1-(2-indanylacetyl)-L-piperidin-2-ylcarbonyl]-L-prolinol,
1-[1-(2-indanylacetyl)-L-piperidin-2-ylcarbonyl]-L-proline,
1-[1-(2-indanylacetyl)-L-piperidin-2-ylcarbonyl]-L-prolinal,
3-[1-(2-indanylacetyl)-DL-piperidin-2-ylcarbonyl]-thiazolidine,
3-[1-(2-indanylacetyl)-L-piperidin-2-ylcarbonyl]-thiazolidine,
3-[1-(2-indanylacetyl)-D-piperidin-2-ylcarbonyl]-thiazolidine,
3-[1-(2-indanylacetyl)-DL-piperidin-2-ylcarbonyl]-L-thioprolinal,
3-[1-(2-indanylacetyl)-L-piperidin-2-ylcarbonyl]-L-thioprolinal,
3-[1-(2-indanylacetyl)-D-piperidin-2-ylcarbonyl]-L-thioprolinal,
1-{1-[5-(indan-2-yl)pentanoyl]-L-piperidin-2-ylcarbonyl}pyrrolidine,
1-{1-[5-(indan-2-yl)pentanoyl]-D-piperidin-2-ylcarbonyl}pyrrolidine,
1-{1-[5-(indan-2-yl)pentanoyl]-L-piperidine-2-ylcarbonyl}-L-prolinal,
1-[4-(2-indanylacetyl)-DL-1,4-thiazan-3-ylcarbonyl]-pyrrolidine,
1-[4-(2-indanylacetyl)-L-1,4-thiazan-3-ylcarbonyl]pyrrolidine,
1-[4-(2-indanylacetyl)-D-1,4-thiazan-3-ylcarbonyl]pyrrolidine,
3-[4-(2-indanylacetyl)-DL-1,4-thiazan-3-ylcarbonyl]-thiazolidine,
3-[4-(2-indanylacetyl)-L-1,4-thiazan-3-ylcarbonyl]-thiazolidine,
3-[4-(2-indanylacetyl)-D-1,4-thiazan-3-ylcarbonyl]-thiazolidine,
1-[4-(2-indanylacetyl)-DL-1,4-thiazan-3-ylcarbonyl]-L-proline methyl ester,
1-[4-(2-indanylacetyl)-L-1,4-thiazan-3-ylcarbonyl]-L-proline methyl ester,
1-[4-(2-indanylacetyl)-DL-1,4-thiazan-3-ylcarbonyl]-L-prolinol,
1-[4-(2-indanylacetyl)-L-1,4-thiazan-3-ylcarbonyl]-L-prolinal,
1-[4-(2-indanylacetyl)-L-1,4-thiazan-3-ylcarbonyl]-L-prolinal,
3-[4-(2-indanylacetyl)-DL-1,4-thiazan-3-ylcarbonyl]-L-thioproline ethyl ester, 3-[4-(2-indanylacetyl)-L-1,4-thiazan-3-ylcarbonyl]-L-thioprolinol,
3-[4-(2-indanylacetyl)-D-1,4-thiazan-3-ylcarbonyl]-L-thioproline,
3-[4-(2-indanylacetyl)-L-1,4-thiazan-3-ylcarbonyl]-L-thioprolinal,
3-{4-[6-(indan-2-yl)hexanoyl]-L-1,4-thiazan-3-ylcarbonyl}thiazolidine,
1-[1-(1,2,3,4-tetrahydronaphthalen-2-ylcarbonyl)-L-prolyl]pyrrolidine,
1-[1-(1,2,3,4-tetrahydronaphthalen-2-ylcarbonyl)-D-prolyl]pyrrolidine,
3-[1-(1,2,3,4-tetrahydronaphthalen-2-ylcarbonyl)-L-prolyl]thiazolidine,
1-[1-(1,2,3,4-tetrahydronaphthalen-2-ylcarbonyl)-L-prolyl]-L-prolinal,
3-[1-(1,2,3,4-tetrahydronaphthalen-2-ylcarbonyl)-L-prolyl]-L-thioprolinal,
3-[1-(1,2,3,4-tetrahydronaphthalen-2-ylacetyl)-L-prolyl]thiazolidine,
3-[1-(1,2,3,4-tetrahydronaphthalen-2-ylacetyl)-D-prolyl]thiazolidine,
1-[3-(1,2,3,4-tetrahydronaphthalen-2-ylcarbonyl)-L-thioprolyl]pyrrolidine,
1-[3-(1,2,3,4-tetrahydronaphthalen-2-ylcarbonyl)-D-thioprolyl]pyrrolidine,
3-[3-(1,2,3,4-tetrahydronaphthalen-2-ylcarbonyl)-L-thioprolyl]thiazolidine,
1-[3-(1,2,3,4-tetrahydronaphthalen-2-ylcarbonyl)-L-thioprolyl]-L-proline,
1-[3-(1,2,3,4-tetrahydronaphthalen-2-ylcarbonyl)-L-thioprolyl]-L-prolinal,
3-[3-(1,2,3,4-tetrahydronaphthalen-2-ylcarbonyl)-L-thioprolyl]-L-thioprolinol,
3-[3-(1,2,3,4-tetrahydronaphthalen-2-ylcarbonyl)-L-thioprolyl]-L-thioprolinal,
3-{3-[3-(1,2,3,4-tetrahydronaphthalen-2-yl)propionyl]-L-thioprolyl}thiazolidine,
1-[1-(1,2,3,4-tetrahydronaphthalen-2-ylacetyl)-L-prolyl]pyrrolidine,
1-[1-(1,2,3,4-tetrahydronaphthalen-2-ylacetyl)-D-prolyl]pyrrolidine,
1-[3-(1,2,3,4-tetrahydronaphthalen-2-ylacetyl)-L-thioprolyl]pyrrolidine,
1-[3-(1,2,3,4-tetrahydronaphthalen-2-ylacetyl)-D-thioprolyl]pyrrolidine,
3-[3-(1,2,3,4-tetrahydronaphthalen-2-ylacetyl)-L-thioprolyl]thiazolidine,
3-[3-(1,2,3,4-tetrahydronaphthalen-2-ylacetyl)-D-thioprolyl]thiazolidine,
1-[1-(1,2,3,4-tetrahydronaphthalen-2-ylcarbonyl)-DL-piperidin-2-ylcarbonyl]pyrrolidine,
1-[1-(1,2,3,4-tetrahydronaphthalen-2-ylcarbonyl)-D-piperidin-2-ylcarbonyl]pyrrolidine,
3-[1-(1,2,3,4-tetrahydronaphthalen-2-ylcarbonyl)-DL-piperidin-2-ylcarbonyl]thiazolidine,
3-[1-(1,2,3,4-tetrahydronaphthalen-2-ylcarbonyl)-L-piperidin-2-ylcarbonyl]thiazolidine,
1-[1-(1,2,3,4-tetrahydronaphthalen-2-ylcarbonyl)-DL-piperidin-2-ylcarbonyl]-L-proline methyl ester,
1-[1-(1,2,3,4-tetrahydronaphthalen-2-ylcarbonyl)-L-piperidin-2-ylcarbonyl]-L-prolinol,
1-[1-(1,2,3,4-tetrahydronaphthalen-2-ylcarbonyl)-L-piperidin-2-ylcarbonyl]-L-prolinal,
3-[1-(1,2,3,4-tetrahydronaphthalen-2-ylcarbonyl)-L-piperidin-2-ylcarbonyl]-L-thioprolinal,
3-[1-(1,2,3,4-tetrahydronaphthalen-2-ylcarbonyl)-D-piperidin-2-ylcarbonyl]-L-thioprolinal,
1-{1-[4-(1,2,3,4-tetrahydronaphthalen-2-yl)butanoyl]-L-piperidin-2-ylcarbonyl}-L-proline,
1-[4-(1,2,3,4-tetrahydronaphthalen-2-ylcarbonyl)-DL-1,4-thiazan-3-ylcarbonyl]pyrrolidine,
1-[4-(1,2,3,4-tetrahydronaphthalen-2-ylcarbonyl)-L-1,4-thiazan-3-ylcarbonyl]pyrrolidine,
3-[4-(1,2,3,4-tetrahydronaphthalen-2-ylcarbonyl)-DL-1,4-thiazan-3-ylcarbonyl]thiazolidine,
3-[4-(1,2,3,4-tetrahydronaphthalen-2-ylcarbonyl)-L-1,4-thiazan-3-ylcarbonyl]thiazolidine,
3-[4-(1,2,3,4-tetrahydronaphthalen-2-ylcarbonyl)-D-1,4-thiazan-3-ylcarbonyl]thiazolidine,
1-[4-(1,2,3,4-tetrahydronaphthalen-2-ylcarbonyl)-DL-1,4-thiazan-3-ylcarbonyl]-L-proline methyl ester,
1-[4-(1,2,3,4-tetrahydronaphthalen-2-ylcarbonyl)-L-1,4-thiazan-3-ylcarbonyl]-L-prolinol,
1-[4-(1,2,3,4-tetrahydronaphthalen-2-ylcarbonyl)-DL-1,4-thiazan-3-ylcarbonyl]-L-proline,
1-[4-(1,2,3,4-tetrahydronaphthalen-2-ylcarbonyl)-L-1,4-thiazan-3-ylcarbonyl]-L-proline,
1-[4-(1,2,3,4-tetrahydronaphthalen-2-ylcarbonyl)-L-1,4-thiazan-3-ylcarbonyl]-L-prolinal,
1-[4-(1,2,3,4-tetrahydronaphthalen-2-ylcarbonyl)-D-1,4-thiazan-3-ylcarbonyl]-L-prolinal,
3-[4-(1,2,3,4-tetrahydronaphthalen-2-ylcarbonyl)-DL-1,4-thiazan-3-ylcarbonyl]-L-thioproline ethyl ester,
3-[4-(1,2,3,4-tetrahydronaphthalen-2-ylcarbonyl)-L-1,4-thiazan-3-ylcarbonyl]-L-thioprolinol,
3-[4-(1,2,3,4-tetrahydronaphthalen-2-ylcarbonyl)-D-1,4-thiazan-3-ylcarbonyl]-L-thioproline,
3-[4-(1,2,3,4-tetrahydronaphthalen-2-ylcarbonyl)-L-1,4-thiazan-3-ylcarbonyl]-L-thioprolinal,
3-[4-(1,2,3,4-tetrahydronaphthalen-2-ylcarbonyl)-D-1,4-thiazan-3-ylcarbonyl]-L-thioprolinal,
3-{4-[6-(1,2,3,4-tetrahydronaphthalen-2-yl)hexanoyl]-L-1,4-thiazan-3-ylcarbonyl}-L-thioprolinal,
1-[1-(2-indenylacetyl)-L-prolyl]pyrrolidine,
1-[1-(2-indenylacetyl)-D-prolyl]pyrrolidine,
3-[1-(2-indenylacetyl)-L-prolyl]thiazolidine,
3-[1-(2-indenylacetyl)-D-prolyl]thiazolidine,
1-[1-(2-indenylacetyl)-L-prolyl]-L-proline methyl ester,
1-[1-(2-indenylacetyl)-L-prolyl]-L-prolinol,
1-[1-(2-indenylacetyl)-L-prolyl]-L-proline,
1-[1-(2-indenylacetyl)-L-prolyl]-L-prolinal,
3-[1-(2-indenylacetyl)-L-prolyl]-L-thioprolinal,
1-{1-[4-(inden-2-yl)butanoyl]-L-prolyl}pyrrolidine,
3-{1-[4-(inden-2-yl)butanoyl]-L-prolyl}-L-thioprolinal,
3-[1-(2-indenylcarbonyl)-L-prolyl]thiazolidine,
1-[3-(2-indenylacetyl)-L-thioprolyl]pyrrolidine,
1-[3-(2-indenylacetyl)-D-thioprolyl]pyrrolidine,
3-[3-(2-indenylacetyl)-L-thioprolyl]thiazolidine,
3-[3-(2-indenylacetyl)-D-thioprolyl]thiazolidine,
1-[3-(2-indenylacetyl)-L-thioprolyl]-L-prolinal,
1-[3-(2-indenylacetyl)-D-thioprolyl]-L-prolinal,
3-[3-(2-indenylacetyl)-L-thioprolyl]-L-thioproline ethyl ester,
3-[3-(2-indenylacetyl)-L-thioprolyl]-L-thioproline,
3-[3-(2-indenylacetyl)-L-thioprolyl]-L-thioprolinal,
3-[3-(2-indenylacetyl)-L-thioprolyl]-L-thioprolinol,
3-{3-[4-(inden-2-yl)butanoyl]-L-thioprolyl}thiazolidine,
1-[1-(2-indenylacetyl)-DL-piperidin-2-ylcarbonyl]pyrrolidine,
1-[1-(2-indenylacetyl)-L-piperidin-2-ylcarbonyl]pyrrolidine,
1-[1-(2-indenylacetyl)-D-piperidin-2-ylcarbonyl]pyrrolidine,
1-[1-(2-indenylacetyl)-L-piperidin-2-ylcarbonyl]-L-prolinal, 1-{1-[5-(inden-2-yl)pentanoyl]-L-piperidin-2-ylcarbonyl}-L-prolinal,
3-[1-(2-indenylacetyl)-DL-piperidin-2-ylcarbonyl]-thiazolidine,
3-[1-(2-indenylacetyl)-L-piperidin-2-ylcarbonyl]-thiazolidine,
3-[1-(2-indenylacetyl)-D-piperidin-2-ylcarbonyl]-thiazolidine,
3-[1-(2-indenylacetyl)-DL-piperidin-2-ylcarbonyl]-L-thioprolinal,
3-[1-(2-indenylacetyl)-L-piperidin-2-ylcarbonyl]-L-thioprolinal,
3-{1-[3-(inden-2-yl)propionyl]-L-piperidin-2-ylcarbonyl}-L-thioprolinal,
1-[4-(2-indenylacetyl)-DL-1,4-thiazan-3-ylcarbonyl]-pyrrolidine,
1-[4-(2-indenylacetyl)-L-1,4-thiazan-3-ylcarbonyl]pyrrolidine,
3-[4-(2-indenylacetyl)-DL-1,4-thiazan-3-ylcarbonyl]-thiazolidine,
3-[4-(2-indenylacetyl)-L-1,4-thiazan-3-ylcarbonyl]-thiazolidine,
1-[4-(2-indenylacetyl)-DL-1,4-thiazan-3-ylcarbonyl]-L-prolinal,
1-[4-(2-indenylacetyl)-L-1,4-thiazan-3-ylcarbonyl]-L-prolinal,
3-[4-(2-indenylacetyl)-L-1,4-thiazan-3-ylcarbonyl]-L-thioprolinal,
3-{4-[4-(inden-2-yl)butanoyl]-L-1,4-thiazan-3-ylcarbonyl}-L-thioprolinal,
3-{4-[5-(inden-2-yl)pentanoyl]-L-1,4-thiazane-3-ylcarbonyl}-L-thioprolinal,
3-{4-[6-(inden-2-yl)hexanoyl]-L-1,4-thiazan-3-ylcarbonyl}-L-thioprolinal,
1-[1-(5-methylindan-2-ylacetyl)-L-prolyl]pyrrolidine,
1-{1-[3-(5-methyl-6-nitroindan-2-yl)propionyl]-L-prolyl}pyrrolidine,
1-[1-(5-amino-6-methylinden-2-ylacetyl)-L-prolyl]pyrrolidine,
1-[1-(6-methoxy-1,2,3,4-tetrahydronaphthalen-2-ylacetyl)-L-prolyl]pyrrolidine,
1-{1-[4-(5-chloro-7-methyl-1,2,3,4-tetrahydronaphthalen-2-yl)butanoyl]-L-prolyl}pyrrolidine,
1-[1-(7-methoxy-2,3,4,5-tetrahydro-1H-benzocyclohepten-2-ylacetyl)-L-prolyl]pyrrolidine,
1-{1-[3-(5-aminoindan-2-yl)propionyl]-D-prolyl}pyrrolidine,
3-[1-(5-methoxyindan-2-ylacetyl)-L-prolyl]-thiazolidine,
3-{1-[6-(6-methoxy-7-methyl-1,2,3,4-tetrahydronaphthalene-2-yl)hexanoyl]-L-prolyl}thiazolidine
3-{1-[3-(7-methoxy-2,3,4,5-tetrahydro-1H-benzocyclohepten-2-yl)propionyl]-L-prolyl}thiazolidine,
3-[1-(6-methoxy-1,2,3,4-tetrahydronaphthalen-2-ylacetyl)-L-prolyl]thiazolidine,
3-{1-[3-(5-methyl-6-nitroinden-2-yl)propionyl]-D-prolyl}thiazolidine,
3-{1-[4-(inden-2-yl)butanoyl]-DL-prolyl}thiazolidine,
1-[3-(5-aminoindan-2-ylacetyl)-L-thioprolyl]pyrrolidine,
1-[3-(5-nitroindan-2-ylacetyl)-L-thioprolyl]pyrrolidine,
1-[3-(5-chloroindan-2-ylacetyl)-L-thioprolyl]pyrrolidine,
1-{3-[4-(indan-2-yl)butanoyl]-L-thioprolyl}pyrrolidine,
1-[3-(5-aminoinden-2-ylacetyl)-L-thioprolyl]pyrrolidine,
1-[3-(6-methoxy-1,2,3,4-tetrahydronaphthalen-2-ylacetyl)-L-thioprolyl}pyrrolidine,
1-[3-(2,3,4,5-tetrahydro-1H-benzocyclohepten-2-ylacetyl)-L-thioprolyl]pyrrolidine,
3-[3-(5,6-dimetylindan-2-ylacethyl)-L-thioprolyl]-thiazolidine,
3-{3-[5-(5-methyl-6-nitroindan-2yl)pentanoyl]-L-thioprolyl}thiazolidine,
3-{3-[4-(5-aminoinden-2-yl)butanoyl]-L-thioprolyl}thiazolidine,
3-{3-[3-(6-methoxy-7-methyl-1,2,3,4-tetrahydronaphthalen-2-yl)propionyl-L-thioprolyl}thiazolidine,
3-[3-(7-methoxy-8-methyl-2,3,4,5-tetrahydro-1H-benzocyclohepten-2-ylacetyl)-L-thioprolyl]thiazolidine,
3-[3-(2,3,4,5-tetrahydro-1H-benzocyclohepten-2-ylacetyl)-D-thioprolyl]thiazolidine,
1-{1-[5-(6-methoxy-1,2,3,4-tetrahydronaphthalen-2-yl)pentanoyl]-DL-piperidin-2-ylcarbonyl}pyrrolidine,
1-[1-(6-chloro-1,2,3,4-tetrahydronaphthalen-2-ylacetyl)-L-piperidin-2-ylcarbonyl]pyrrolidine,
3-[3-(6-methoxy-1,2,3,4-tetrahydronaphthalen-2-ylacetyl)-L-thioprolyl]thiazolidine,
3-{1-[6-(7-amino-8-methyl-2,3,4,5-tetrahydro-1H-benzocyclohepten-2yl)hexanoyl]-DL-piperidin-2-ylcarbonyl}thiazolidine,
1-[1-(1,2,3,4-tetrahydronaphthalen-2-ylacetyl)-L-piperidin-2-ylcarbonyl]pyrrolidine,
3-[1-(1,2,3,4-tetrahydronaphthalen-2-ylacetyl)-L-piperidin-2-ylcarbonyl]thiazolidine
3-{1-[5-(7,8-dimethyl-2,3,4,5-tetrahydro-1H-benzocyclohepten-2-yl)pentanoyl]-D-piperidin-2-ylcarbonyl}thiazolidine,
1-{4-[3-(1,2,3,4-tetrahydronaphthalen-2-yl)propionyl]-L-1,4-thiazan-3-ylcarbonyl}pyrrolidine,
1-{4-[4-(7-methoxy-8-methyl-2,3,4,5-tetrahydro-1H-benzocyclohepten-2-yl)butanoyl]-D-1,4-thiazan-3-ylcarbonyl}pyrrolidine,
3-{4-[4-(5-methoxy-6-methylinden-2-yl)butanoyl]-L-1,4-thiazan-3-ylcarbonyl}thiazolidine,
3-{4-[4-(5-nitroindan-2-yl)butanoyl]-D-1,4-thiazan-3-ylcarbonyl}thiazolidine,
1-{1-[(S)-(−)-1,2,3,4-tetrahydronaphthalen-2-ylacetyl]-L-prolyl}pyrrolidine,
1-{1-[(R)-(+)-1,2,3,4-tetrahydronaphthalen-2-ylacetyl]-L-prolyl}pyrrolidine,
3-{1-[(S)-(−)-1,2,3,4-tetrahydronaphthalen-2-ylacetyl]-L-prolyl}thiazolidine,
3-{1-[(R)-(+)-1,2,3,4-tetrahydronaphthalen-2-ylacetyl]-L-prolyl}thiazolidine,
1-{3-[(S)-(−)-1,2,3,4-tetrahydronaphthalen-2-ylacetyl]-L-thioprolyl}pyrrolidine,
1-{3-[(R)-(+)-1,2,3,4-tetrahydronaphthalen-2-ylacetyl]-L-thioprolyl}pyrrolidine,
3-{3-[(S)-(−)-1,2,3,4-tetrahydronaphthalen-2-ylacetyl]-L-thioprolyl}thiazolidine,
3-{3-[(R)-(+)-1,2,3,4-tetrahydronaphthalen-2-ylacetyl]-L-thioprolyl}thiazolidine,
1-{3-[(S)-(−)-1,2,3,4-tetrahydronaphthalen-2-ylacetyl]-D-thioprolyl}pyrrolidine,
1-{3-[(R)-(+)-1,2,3,4-tetrahydronaphthalen-2-ylacetyl]-D-thioprolyl}pyrrolidine,
1-{1-[(S)-(−)-1,2,3,4-tetrahydronaphthalen-2-ylacetyl]-L-piperidin-2-ylcarbonyl}pyrrolidine,
3-{1-[(R)-(+)-1,2,3,4-tetrahydronaphthalen-2-ylacetyl]-L-piperidin-2-ylcarbonyl}thiazolidine,
1-[1-(2-indanylcarbonyl)-L-prolyl]-L-proline methyl ester,
1-[1-(1,2,3,4-tetrahydronaphthalen-2-ylacetyl)-L-prolyl]-L-proline methyl ester, 1-[1-(2,3,4,5-tetrahydro-1H-benzocyclohepten-2-ylacetyl)-L-prolyl]-L-proline methyl ester,
3-{1-[5-(5-chloroindan-2-yl)pentanoyl]-L-prolyl}-L-thioproline ethyl ester,
1-[3-(5-methoxyinden-2-ylacetyl)-L-thioprolyl]-L-proline methyl ester,
3-{1-[6-(6-methoxy-7-methyl-1,2,3,4-tetrahydronaphthalene-2-yl)hexanoyl]-L-prolyl}-L-thioproline ethyl ester,
3-[3-(2-indanylacetyl)-L-thioprolyl]-L-thioproline ethyl ester,
3-{1-[4-(5-amino-6-methylinden-2-yl)butanoyl]-L-prolyl}-L-thioproline ethyl ester,
3-{3-[5-(7-amino-8-methyl-2,3,4,5-tetrahydro-1H-benzocyclohepten-2-yl)pentanoyl]-L-thioprolyl}-L-thioproline ethyl ester,
1-{3-[6-(6,7-dimethyl-1,2,3,4-tetrahydronaphthalen-2-yl)hexanoyl]-D-thioprolyl}-L-proline methyl ester,
1-{1-[5-(5-aminoinden-2-yl)pentanoyl]-DL-piperidin-2-ylcarbonyl}-L-proline methyl ester,
3-{1-[4-(7-chloro-8-methyl-2,3,4,5-tetrahydro-1H-benzocyclohepten-2-yl)butanoyl]-DL-piperidine-2-ylcarbonyl}-L-thioproline ethyl ester,
1-{1-[5-(6-nitro-7-methyl-1,2,3,4-tetrahydronaphthalen-2-yl)pentanoyl]-L-piperidin-2-ylcarbonyl}-L-proline methyl ester,
1-{1-[3-(5-methoxy-6-methylindan-2-yl)propionyl]-L-piperidin-2-ylcarbonyl}-L-proline ethyl ester,
3-{1-[6-(inden-2-yl)hexanoyl]-L-piperidin-2-ylcarbonyl}-L-thioproline ethyl ester,
1-{4-[6-(5-methoxyindan-2-yl)hexanoyl]-DL-1,4-thiazan-3-ylcarbonyl}-L-proline methyl ester,
1-[4-(7-methoxy-2,3,4,5-tetrahydro-1H-benzocycloheptene-2-ylacetyl)-L-1,4-thiazan-3-ylcarbonyl]-L-proline methyl ester,
1-{4-[4-(indan-2-yl)butanoyl]-DL-1,4-thiazane-3-ylcarbonyl}-L-proline,
1-{4-[5-(7,8-dimethyl-2,3,4,5-tetrahydro-1H-benzocyclohepten-2-yl)pentanoyl]-DL-1,4-thiazan-3-ylcarbonyl}-L-proline,
1-[1-(1,2,3,4-tetrahydronaphthalen-2-ylacetyl)-L-prolyl]-L-prolinol,
1-[1-(2,3,4,5-tetrahydro-1H-benzocyclohepten-2-ylacetyl)-L-prolyl]-L-prolinol,
3-{1-[3-(5-nitroindan-2-yl)propionyl]-L-prolyl}-L-thioprolinol,
3-{1-[6-(5-amino-6-methylindan-2-yl)hexanoyl]-L-prolyl}-L-thioprolinol,
3-[1-(5-chloro-7-methyl-1,2,3,4-tetrahydronaphthalen-2-ylcarbonyl)-L-prolyl]-L-thioprolinol,
1-[3-(2-indanylacetyl)-L-thioprolyl]-L-prolinol,
1-[3-(1,2,3,4-tetrahydronaphthalen-2-ylacetyl)-L-thioprolyl]-L-prolinol,
1-{3-[5-(5-methoxyindan-2-yl-)pentanoyl]-D-thioprolyl}-L-prolinol,
3-[3-(7-chloro-8-methyl-2,3,4,5-tetrahydro-1H-benzocyclohepten-2-ylcarbonyl)-L-thioprolyl]-L-thioprolinol,
3-{1-[3-(5-nitroinden-2-yl)propionyl]-DL-piperidin-2-ylcarbonyl}-L-thioprolinol,
3{1-[6-(6-methyl-7-nitro-1,2,3,4-tetrahydronaphthalen-2-yl)hexanoyl]-L-piperidin-2-ylcarbonyl}-L-thioprolinol,
1-{4-[5-(7,8-dimethyl-2,3,4,5-tetrahydro-1H-benzocyclohepten-2-yl)pentanoyl]-DL-1,4-thiazan-3-ylcarbonyl}-L-prolinol,
3-{4-[5-(5,6-dimethylinden-2-yl)pentanoyl]-L-1,4-thiazane-3-ylcarbonyl}-L-thioprolinol,
1-[1-(5,6-dimethylindan-2-ylacetyl)-L-prolyl]-L-prolinal,
1-[1-(4-methyl-5-nitroindan-2-ylacetyl)-L-prolyl]-L-prolinal,
1-[1-(1,2,3,4-tetrahydronaphthalen-2-ylacetyl)-L-prolyl]-L-prolinal,
1-[1-(2,3,4,5-tetrahydro-1H-benzocyclohepten-2-ylacetyl)-L-prolyl]-L-prolinal,
1-{3-[5-(4-aminoinden-2-yl)pentanoyl]-L-thioprolyl}-L-prolinal,
1-[3-(2,3,4,5-tetrahydro-1H-benzocyclohepten-2-ylcarbonyl)-L-thioprolyl]-L-prolinal,
3-(3-[3-(6-nitro-1,2,3,4-tetrahydronaphthalen-2-yl)-propionyl]-L-thioprolyl}-L-thioprolinal,
3-{3-[4-(6-nitro-2,3,4,5-tetrahydro-1H-benzocyclohepten-2-yl)butanoyl]-L-thioprolyl}-L-thioprolinal,
1-{1-[6-(5-methoxy-6-methylinden-2-yl)hexanoyl]-DL-piperidin-2-ylcarbonyl}-L-prolinal,
1-{1-[4-(7,8-dimethyl-2,3,4,5-tetrahydro-1H-benzocyclohepten-2-yl)butanoyl]-DL-piperidine-2-ylcarbonyl}-L-prolinal,
1-{1-[4-(7-methoxy-8-methyl-2,3,4,5-tetrahydro-1H-benzocyclohepten-2-yl)butanoyl]-D-piperidine-2-ylcarbonyl}-L-prolinal,
3-[4-(7-amino-6-methyl-1,2,3,4-tetrahydronaphthalen-2-ylacetyl)-D-1,4-thiazan-3-ylcarbonyl]-L-thioprolinal The compound (I) of the present invention prepared by the manner discussed above exhibits prolyl endopeptidase inhibitory activity, anti-hypoxic activity, and anti-amnesic activity at the same time, and is a highly safe compound. It is therefore useful as a medicine for treating or preventing cerebral circulation disorder, cerebral metabolism disorder, and memory disturbance.

The compound of formula (I) of the present invention can be prepared in various dosing forms for oral or non-oral administration by formulating various pharmacologically acceptable carriers. When this compound is prepared in dosing forms for oral administration, it is appropriately formulated together with suitable additives, including excipients such as lactose, mannitol, corn starch, crystallized cellulose, etc., binders such as cellulose derivatives, gum arabic, gelatin, etc., disintegrators such as calcium carboxymethyl cellulose, etc., lubricants such as talc, magnesium stearate, etc., and the like. These may be formed into tablets, granules, powders, or capsules. These solid formulations can also be prepared in enteric coated pills using a coating substrate such as hydroxypropylmethyl cellulose phthalate, hydroxypropylmethyl cellulose acetate succinate, cellulose acetate phthalate, methacrylate copolymer, or the like. Non-oral dosing forms include an injection, into which water, ethanol, glycerol, commonly used surface active agents, and the like may be formulated. The compound of formula (I) can also be prepared in a suppository using a suitable suppository substrate.

The amount of dosage of the compound of formula (I) used may vary depending on the body weight, age, symptoms of the subject, the intended treatment effect, the manner by which it is administered, and the period of administration. A generally appropriate amount may be from 1 to 2,000 mg per day, preferably from 10 to 200 mg per day, with the frequency of administration being 1 to 3 times per day.

Hereinafter are presented pharmacological experimental examples to further illustrate the effectiveness of the compound of formula (I). These examples are given for illustration of the invention and are not intended to be limiting thereof.

EXPERIMENTAL EXAMPLES

Experimental Example 1

Inhibitory Activity Against Prolyl Endopeptidase From Brain

A prolyl endopeptidase was prepared from canine brains according to the method of Yoshimoto et al. [J. Biochem., 94, 325 (1983)].

Following buffer solutions were used for the measurement.

Buffer A: 20 mM Tris-HCl buffer (pH 7.0)
Buffer B: Buffer A containing 0.1% gelatin, 1 mM EDTA, and 1 mM 2-mercaptoethanol The prolyl endopeptidase was dissolved in the Buffer B at a concentration of 0.4 unit/ml. This solution (50 μl) was added to 940 μl of the Buffer A, and the solution thus obtained was left at 37° C. for 10 minutes (This solution is herein referred to as "Enzyme solution"). A mixed solution of 50 μl of the Buffer B and 940 μl of Buffer A was used as a "Correction solution".

A test compound was dissolved in dimethylsulfoxide, and 10 μl of the solution was added to the Enzyme solution. The mixture was stirred and allowed to stand at 37° C. for 10 minutes. Separately, 10 μl of dimethylsulfoxide was added to the Enzyme solution and was processed in the same manner. The solution thus obtained was served as a "Control solution". The same procedure was carried out on the Correction solution.

One hundred (100) μl of 2.5 mM benzyloxycarbonylglycylprolylparanitroanilide, which was dissolved with 40% dioxane, was added to each of the above 3 solutions, i.e., the Enzyme solution with the test compound, Control solution, and Correction solution, and the reaction was carried out at 37° C. for 10 minutes.

After the addition of 100 μl of a reaction termination solution [50% acetic acid containing 10% Triton X-100], absorbances of the samples at 410 nm were measured using a spectrophotometer.

Enzyme activities were determined by subtracting the blank value, i.e., the absorbance measured on the Correction solution, from the absorbance of each of the sample solutions and of the Control solution.

Inhibition potency ($IC_{50}$) of the sample compound against prolyl endopeptidase was determined as the concentration of the compound (M) capable of inhibiting 50% of the enzyme activity of the control. The results are shown in Table 1.

TABLE 1

| Compounds | Inhibition Potency, $IC_{50}$ (M) |
|---|---|
| Compound of Example 1 | $6.5 \times 10^{-9}$ |
| Compound of Example 3 | $7.9 \times 10^{-9}$ |
| Compound of Example 4 | $1.4 \times 10^{-8}$ |
| Compound of Example 5 | $2.2 \times 10^{-8}$ |
| Compound of Example 10 | $4.9 \times 10^{-8}$ |
| Compound of Example 14 | $1.8 \times 10^{-8}$ |
| Compound of Example 18 | $4.3 \times 10^{-8}$ |
| Compound of Example 22 | $6.2 \times 10^{-9}$ |
| Compound of Example 42 | $1.3 \times 10^{-9}$ |
| SUAM 1221* | $7.6 \times 10^{-8}$ |
| Aniracetam | $> 10^{-3}$ |

*The compound described in European Patent Publication No. 232849.

Experimental Example 2

Anti-Hypoxic Activity

Groups of ICR male mice (Charles River Co.), age 4 to 5 weeks, each group consisting of 10 mice and each mouse having been fasted for 24 hours, were used for the test. Mice were placed in a transparent desiccator (diameter: 19 cm, height: 30 cm) made of synthetic resin and having 2 valves, one at the upper portion and the other at the lower portion, for replacing the gas therein. A mixed gas (4% $O_2$ + 96% $N_2$) was fed from the upper valve at a rate of 10 l/min to measure the period of time until respiratory arrest took place for each mouse. The time measured was taken as the survival time.

Each tested compound suspended in an solvent was intraperitoneally administered 30 minutes before the start of the mixed gas feeding. A group of mice to which only the solvent was intraperitoneally administered was used as a control.

The anti-hypoxic activity was determined according to the following formula, $$\text{Anti-hypoxic Activity (\%)} = \frac{\text{Survival time of the group to which a test compound was administered}}{\text{Survival time of the control group}} \times 100$$

The results are shown in Table 2.

TABLE 2

| Compounds | Dose (mg/kg) | Anti-hypoxic Activity (%) |
|---|---|---|
| Control | — | 100 |
| Compound of Example 1 | 100 | 131 |
| Compound of Example 2 | 100 | 127 |
| Compound of Example 4 | 100 | 141 |
| Compound of Example 11 | 50 | 141 |
| Compound of Example 17 | 100 | 137 |
| Compound of Example 19 | 100 | 155 |
| Compound of Example 24 | 100 | 235 |
| Compound of Example 26 | 100 | 291 |
| Compound of Example 42 | 100 | 168 |
| Aniracetam | 100 | 115 |
| Aniracetam | 300 | 159 |
| Calcium hopantenate | 250 | 135 |
| Idebenone | 100 | 140 |

As shown in Tables 1 and 2, the compounds of this invention are superior to aniracetam, calcium hopantenate, indebenone, and SUAM 1221 (the compound described in European Patent Publication No. 232849), in their prolyl endopentidase inhibitory activities against the prolyl endopeptidase from canine brain and anti-hypoxic activities.

Experimental Example 3

Anti-Amnesic Activity

Compounds of this invention were checked with respect to their abilities to prevent the inhibition of long-term memory fixation by electric convulsive shock (ECS). CD female rats (Charles River), weighed 160-180 g were used for the test. One hour after the administration of a compound of this invention, the acquisition trial according to the passive avoidance training was performed on the rats. A foot shock was given to the rats when they entered into a dark room. Immediately after that an amnesic treatment by ECS or a sham amnesic treatment was performed. Twenty four (24) hours after the acquisition trial the retention trial was performed. Latency of the mouse entering into a dark room was measured. The results are shown in Table 3.

TABLE 3

| Tested Substance (P.O.) | Amnesic Treatment | Latency to entering into a dark room (sec) |
| --- | --- | --- |
| Solvent | Sham Treatment | 133.0 |
| Solvent | ECS | 0.8 |
| Compound of Ex. 1 (30 mg/kg) | ECS | 77.0 |

Experimental Example 4

Toxicity Experiment

Intraperitoneal administration

Groups of ICR male mice (Charles River Co.), age 4 to 5 weeks, each group consisting of 10 mice were used for the test. A dose of 300 mg/kg of each compound prepared in Examples 1–52 hereinbelow suspended in 5% gum arabic was intraperitoneally administered to each group of mice. No fatal problem in mice was observed during a period of 7 days.

Oral administration

Groups of Fisher 344 male rats, age 6 weeks, each group consisting of 5 rats were used for the test. A dose of 100, 200, 400, and 800 mg/kg of each of the compounds prepared in Examples 1–4, each suspended in 10% gum arabic was chroniaclly administered (P. O.) to each group of rats for 14 days. No fatal problem was observed during a 14 day continuous period during which the compounds were administered.

Hereinafter are presented preparation examples of the compounds of the present invention (Examples) and their intermediates, N-substituted amino acid derivatives (II) (Reference Examples). These examples are given for illustration of the invention and are not intended to be limiting thereof.

PREPARATION EXAMPLES

Reference Example 1

3-(2-indanylacetyl)-L-thioproline ethyl ester

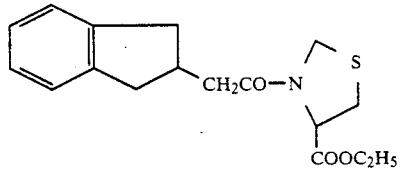

1.4 g of 2-indanylacetic acid and 1.9 g of WSC.HCl were added to 15 ml of methylene chloride under ice-cooling. The mixture was stirred for 5 minutes at room temperature. After an addition of 1.3 g of L-thioproline ethyl ester dissolved in 10 ml of methylene chloride, the mixture was stirred for 5 hours. The reaction mixture was washed with water, diluted hydrochloric acid, and saturated sodium hydrogen carbonate in this order. The organic layer was dried over anhydrous magnesium sulfate, and the solvent was evaporated under reduced pressure. The residue thus obtained was purified by silica gel column chromatography to produce 1.45 g of 3-(2-indanylacetyl)-L-thioproline ethyl ester as a colorless oil (yield: 57%).

IR(neat) cm$^{-1}$: 2940, 1735, 1650, 1400

NMR(CDCl$_3$) δ: 1.23(3H, t, J=6 Hz), 2.00–3.40(9H, m), 4.10(2H, q, J=6 Hz), 4.37(2H, brs), 4.97(1H, t, J=4 Hz), 6.93(4H, s)

Reference Example 2

To a solution of 1.45 g of 3-(2-indanylacetyl)-L-thioproline ethyl ester prepared in Reference Example 1 in 17 ml of ethanol was added 28 ml of 1 N sodium hydroxide, and the mixture was stirred at room temperature. After 1 hour, ethanol was evaporated under reduced pressure. Twenty (20) ml of water was added to the residue and the solution was washed with ethyl acetate. The water layer was acidified with the addition of diluted hydrochloric acid and extracted with ethyl acetate. The organic layer was washed with water and dried over anhydrous magnesium sulfate. After evaporation of the solvent under reduced pressure, the residue was recrystallized from a mixed solvent of ethyl acetate and n-hexane to produce 0.76 g of 3-(2-indanylacetyl)-L-thioproline (yield: 57%).

mp 152°–154° C.

IR(KBr) cm$^{-1}$: 2900, 1720, 1600, 1430, 1220, 730

NMR(CDCl$_3$) δ: 2.07–3.23(8H, m), 4.00–5.17(4H, m), 7.10(4H, s)

Reference Example 3

Colorless crystals of 1-(2-indanylacetyl)-L-proline methyl ester were prepared in the same manner as in Reference Example 1, except that L-proline methyl ester was used instead of L-thioproline ethyl ester (yield: 76%).

mp 71°–73° C.

IR(KBr) cm$^{-1}$: 2850–3070, 1745, 1645, 1430, 1195, 1170, 745

NMR(CDCl$_3$) δ: 1.65–3.75(13H, m), 3.67(3H, s), 4.14–4.67(1H, m), 7.07(4H, s)

Reference Example 4

In the same manner as in Reference Example 2, colorless crystals of 1-(2-indanylacetyl)-L-proline were prepared by hydrolyzing 1-(2-indanylacetyl)-L-proline methyl ester prepared in Reference Example 3. (yield: 89%).

mp 97°–99° C.

IR(KBr) cm$^{-1}$: 2500–3460, 1730, 1600, 1440, 1315, 1180, 740

NMR(CDCl$_3$) δ: 1.51–3.81(13H, m), 4.19–4.67(1H, m), 7.04(4H, s), 9.92(1H, s)

Reference Example 5

Colorless crystals of methyl 4-(2-indanylacetyl)-DL-1,4-thiazan-3-ylcarboxylate were prepared in the same manner as in Reference Example 1, except that methyl DL-1,4-thiazan-3-ylcarboxylate was used instead of L-thioproline ethyl ester (yield: 49%).

mp 77°–79° C.

IR(KBr) cm$^{-1}$: 2940, 1741, 1653, 1417, 1337, 1229, 1194, 1012

NMR(CDCl$_3$) δ: 2.30–2.76(7H, m), 2.76–3.02(2H, m), 3.02–3.25(2H, m), 3.45–3.60(1H, m), 3.76(3H, s), 3.93–4.07(1H, m), 5.67–5.83(1H, m), 7.00–7.27(4H, m)

Reference Example 6

In the same manner as in Reference Example 2, colorless crystals of 4-(2-indanylacetyl)-DL-1,4-thiazan-3-ylcarboxylic acid indanylacetyl)-DL-1,4-thiazan-3-ylcarboxylate prepared in Reference Example 5 (yield: 91%).

mp 65°-68° C.

IR(KBr) cm$^{-1}$: 2910, 1725, 1600, 1420, 1310, 1285, 1180

NMR(CDCl$_3$) δ: 2.30-3.24(11H, m), 3.46-3.66(1H, m), 3.89-4.06(1H, m), 4.93-5.46(1H, m), 5.69-5.83(1H, m), 7.00-7.23(4H, m)

Reference Example 7

Colorless crystals of ethyl 4-(2-indanylacetyl)-DL-1,4-thiazan-3-ylcarboxylate were prepared in the same manner as in Reference Example 1, except that ethyl DL-1,4-thiazan-3-ylcarboxylate was used instead of L-thioproline ethyl ester (yield: 64%).

mp 82°-84° C.

IR(KBr) cm$^{-1}$: 2925, 1735, 1645, 1410, 1365, 1285, 1225, 1185, 1025

NMR(CDCl$_3$) δ: 1.30 (3H, t, J=7 Hz), 2.33-3.25(11H, m), 3.50-3.66(1H, m), 3.95-4.08(1H, m), 4.25(2H, q, J=7 Hz), 5.72-5.80(1H, m), 7.06-7.24(4H, m)

Reference Example 8

A colorless oil of ethyl 1-(2-indanylacetyl)-DL-piperidin-2-ylcarboxylate was prepared in the same manner as in Reference Example 1, except that ethyl DL-piperidin-2-ylcarboxylate was used instead of L-thioproline ethyl ester (yield: 51%).

IR(neat) cm$^{-1}$: 2950, 1730, 1640, 1420, 740

NMR(CDCl$_3$) δ: 1.27(3H, t, J=7 Hz), 1.33-1.72(5H, m), 2.24-3.28(9H, m), 3.71-3.76(1H, m), 4.18(2H, q, J=7 Hz), 5.39-5.41(1H, m), 7.09-7.20(4H, m)

Reference Example 9

Colorless crystals of 1-(2-indanylacetyl)-DL-piperidin-2-ylcarboxylic acid were prepared by hydrolyzing ethyl 1-(2-indanylacetyl)-DL-piperidin-2-ylcarboxylate prepared in Reference Example 8 in the same manner as in Reference Example 2 (yield: 60%).

mp 147°-148° C.

IR(KBr) cm$^{-1}$: 2950, 1740, 1590, 750

NMR(CDCl$_3$) δ: 1.37-1.74(5H, m), 2.28-3.27(9H, m), 3.72-3.77(1H, m), 5.43-5.45(1H, m), 7.09-7.19(4H, m)

Reference Example 10

To a solution of 1.29 g of L-piperidin-2-ylcarboxylic acid in 20 ml of 1 N sodium hydroxide was added 10 ml of water and the solution was ice-cooled. To the solution, 1.94 g of 2-indanylacetyl chloride in 10 ml of benzene was added dropwise with stirring. Then, 10 ml of 1 N sodium hydroxide was added and the mixture was stirred at room temperature overnight. The reaction mixture was washed twice with ether. The water layer was acidified with a concentrated hydrochloric acid under ice-cooling and extracted with ethyl acetate. The organic layer was washed with brine and dried over anhydrous sodium sulfate. After evaporating the solvent under reduced pressure, the residue was recrystallized from ethyl acetate to produce 1.8 g of 1-(2-indanylacetyl)-L-piperidin-2-ylcarboxylic acid as colorless crystals (yield: 62%).

mp 152°-153° C.

IR(KBr) cm$^{31\ 1}$: 2950, 1740, 1590, 750

NMR(CDCl$_3$) δ: 1.39-1.71(5H, m), 2.28-3.27(9H, m), 3.73-3.77(1H, m), 5.41-5.42(1H, m), 7.10-7.20(4H, m)

Reference Example 11

Colorless crystals of 1-(2-indanylacetyl)-D-piperidin-2-ylcarboxylic acid were prepared in the same manner as in Reference Example 10, except that D-piperidin-2-ylcarboxylic acid was used instead of L-piperidin-2-ylcarboxylic acid (yield: 71%).

mp 152°-153° C.

IR(KBr) cm$^{-1}$: 2950, 1740, 1590, 750

NMR(CDCl$_3$) δ: 1.41-1.71(5H, m), 2.27-3.27(9H, m), 3.73-3.77(1H, m), 5.39-5.41(1H, m), 7.10-7.20(4H, m)

Reference Example 12

1-(1,2,3,4-tetrahydronaphthalen-2-ylcarbonyl)-L-proline methyl ester

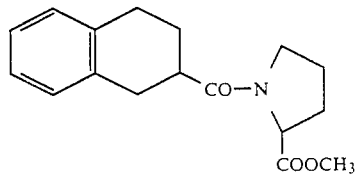

A colorless oil of 1-(1,2,3,4-tetrahydronaphthalen-2-ylcarbonyl)-L-proline methyl ester was prepared in the same manner as Reference Example 1, except that 1,2,3,4-tetrahydronaphthalen-2-ylcarboxylic acid was used instead of 2-indanylacetic acid and L-proline methyl ester was used instead of L-thioproline ethyl ester (yield: 63%).

IR(neat) cm$^{-1}$: 2840-3050, 1740, 1640, 1430, 1195, 1170, 745

NMR(CDCl$_3$) δ: 1.54-2.32(6H, m), 2.53-3.60(7H, m), 3.65(3H, s), 4.27-4.60(1H, m), 6.94(4H, s)

Reference Example 13

In the same manner as in Reference Example 2, a colorless viscous oil 1-(1,2,3,4-tetrahydronaphthalen-2-ylcarbonyl)-L-proline methyl ester was prepared by hydrolyzing 1-(1,2,3,4-tetrahydronaphthalen-2-ylcarbonyl)-L-proline prepared in Reference Example 12 (yield: 86%).

IR(neat) cm$^{-1}$: 2570-3420, 1735, 1600, 1450, 740

NMR(CDCl$_3$) δ: 1.61-2.40(6H, m), 2.55-3.09(5H, m), 3.43-3.85(2H, m), 4.43-4.77(1H, m), 7.08(4H, s), 10.49(1H, s)

Reference Example 14

To a solution of 3.4 g of 1,2,3,4-tetrahydronaphthalen-2-ylacetic acid in 50 ml of methylene chloride was added 14.1 g of WSC.HCl with stirring at room temperature. Then, 3.6 g of L-proline methyl ester hydrochloride and 2.2 g of triethylamine were added to the solution. The mixture was stirred for 17 hours at room temperature. The reaction mixture was washed with water, diluted hydrochloric acid, and saturated sodium hydrogen carbonate in this order. The organic layer was dried over anhydrous magnesium sulfate, and the solvent was evaporated under reduced pressure to obtain 3.6 g of 1-(1,2,3,4-tetrahydronaphthalen-2-ylacetyl)-L-proline methyl ester as a colorless oil.

3.6 g of this oily substance was dissolved in 40 ml of ethanol and 70 ml of 1 N sodium hydroxide was added to the solution. The mixture was stirred at room temperature. After 30 minutes, ethanol was evaporated under reduced pressure and the residue was washed with ethyl acetate. The water layer was acidified with diluted hydrochloric acid and extracted with ethyl acetate. The organic layer was washed with water and dried over anhydrous sodium sulfate. After evaporating the solvent under reduced pressure, an oily substance obtained was purified by silica gel column chromatography to produce 1.7 g of 1-(1,2,3,4-tetrahydronaphthalen-2-ylacetyl)-L-proline as clorless crystals (yield: 32%).

mp 112°-134° C.

IR(KBr) cm⁻¹: 2450-3200, 1745, 1710, 1605, 1450, 760, 750

NMR(CDCl₃) δ: 1.40-1.55(1H, m), 1.97-2.96(12H, m), 3.47-3.66(2H, m), 4.58(1H, d, J=8 Hz), 7.06(4H, s), 7.87(1H, brs)

Reference Example 15

1-(2-indenylacetyl)-L-proline methyl ester

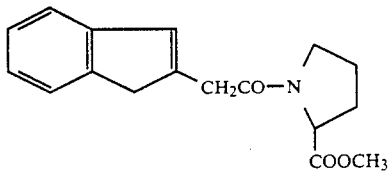

Colorless crystals of 1-(2-indenylacetyl)-L-proline methyl ester were prepared in the same manner as Reference Example 1, except that 2-indenylacetic acid was used instead of 2-indanylacetic acid and L-proline methyl ester was used instead of L-thioproline ethyl ester (yield: 81%).

mp 113°-115° C.

IR(KBr) cm⁻¹: 2890-3080, 1745, 1645, 1430, 1195, 1170, 750, 715

NMR(CDCl₃) δ: 1.90-2.22(4H, m), 3.45(2H, s), 3.56(2H, s), 3.73(3H, s), 3.42-3.76(2H, m), 4.48-4.53(1H, m), 6.70(1H, s), 7.09-7.40(4H, m)

Reference Example 16

In the same manner as in Reference Example 2, colorless crystals of 1-(2-indenylacetyl)-L-proline was prepared by hydrolyzing 1-(2-indenylacetyl)-L-proline methyl ester prepared in Reference Example 15 (yield: 79%).

mp 185°-186° C.

IR(KBr) cm⁻¹: 2400-3080, 1710, 1610, 1590, 1460, 1255, 760, 750, 715

NMR(CDCl₃) δ: 1.93-2.21(4H, m), 3.45(2H, s), 3.58(2H, s), 3.43-3.71(2H, m), 4.45-4.53(1H, m), 4.60-5.80(1H, br), 6.71(1H, s), 7.09-7.39(4H, m)

Reference Example 17

3-(1,2,3,4-tetrahydronaphthalen-2-ylacetyl)-L-thioproline ethyl ester

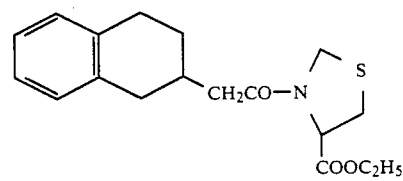

To a mixture of 2.85 g of 1,2,3,4-tetrahydronaphthalen-2-ylacetic acid and 13.45 g of WSC.HCl was added 45 ml of methylene chloride under ice-cooling. The mixture was stirred for 5 minutes at room temperature. To this was added a solution of 2.4 g of L-thioproline ethyl ester in 7 ml of methylene chloride at room temperature, and the mixture was stirred for a further 18 hours at the same temperature. The reaction mixture was washed with water, diluted hydrochloric acid, and saturated sodium hydrogen carbonate in this order. The organic layer was dried over anhydrous magnesium sulfate, and the solvent was evaporated under reduced pressure. The residue thus obtained was purified by silica gel column chromatography to produce 3.4 g of 3-(1,2,3,4-tetrahydronaphthalen-2-ylacetyl)-L-thioproline ethyl ester as a colorless oil (yield: 68%).

IR(neat) cm⁻¹: 2925, 1745, 1645, 1400, 740

NMR(CDCl₃) δ: 1.19-3.20(14H, m), 4.11-5.20(5H, m), 6.94-7.22(4H, m)

Reference Example 18

To a solution of 2.0 g of 3-(1,2,3,4-tetrahydronaphthalen-2-ylacetyl)-L-thioproline ethyl ester prepared in Reference Example 17 in 23 ml of ethanol was added 37 ml of 1 N sodium hydroxide at room temperature, and the mixture was stirred at the same temperature. After 3 hours, ethanol was evaporated under reduced pressure. After the addition of 100 ml of water and washing with benzene, the water layer was acidified with the addition of diluted hydrochloric acid and extracted with ethyl acetate. The organic layer was washed with brine and dried over anhydrous magnesium sulfate. After evaporation of the solvent under reduced pressure, the residue was treated with isopropyl ether to produce 1.5 g of colorless crystals of 3-(1,2,3,4-tetrahydronaphthalen-2-ylacetyl)-L-thioproline (yield: 82%).

mp 120°-125° C.

IR(KBr) cm⁻¹: 2925, 1725, 1580, 1450, 730

NMR(CDCl₃) δ: 1.36-1.60(1H, m), 1.86-2.10(1H, m), 2.16-3.46(9H, m), 4.40-5.17(3H, m), 6.82-7.34(4H, m) 8.74-9.15(1H, br)

Reference Example 19

Colorless crystals of 3-(2-indenylacetyl)-L-thioproline were prepared in the same manner as Reference Example 10, except that 2-indenylacetyl chloride and L-thioproline were used instead of 2-indanylacetyl chloride and L-piperidin-2-ylcarboxylic acid, respectively (yield: 44%).

mp 137.0°-137.5° C.

IR(KBr) cm⁻¹: 1655, 1635, 1445, 1400, 920

NMR(CDCl₃) δ: 1.86-2.04(4H, m), 3.12-3.89(10H, m), 4.72(2H, s), 5.05(1H, t, J=7 Hz), 6.72(1H, s), 7.13-7.41(4H, m)

Reference Example 20

1-(6-methoxy-1,2,3,4-tetrahydronaphthalen-2-ylacetyl)-L-proline methyl ester

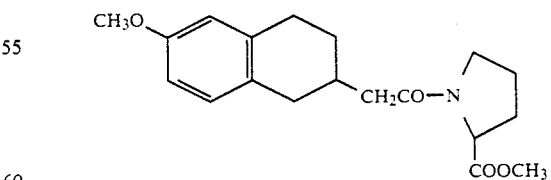

1-(6-methoxy-1,2,3,4 tetrahydronaphthalen-2-ylacetyl)-L-proline methyl ester was prepared as an oily substance in the same manner as Reference Example 1, except that 6-methoxy-1,2,3,4-tetrahydronaphthalen-2-ylacetic acid and L-proline methyl ester were used instead of 2-indanylacetic acid and L-thioproline ethyl este respectively (yield: 79%).

IR(neat) cm$^{-1}$: 2825–3000, 1735, 1630, 1165, 1030
NMR(CDCl$_3$) δ: 1.30–2.96(13H, m), 3.41–3.81(8H, m), 4.33–4.60(1H, m), 6.60–6.71(2H, m), 6.89–7.00(1H, m)

Reference Example 21

In the same manner as in Reference Example 2, colorless crystals of 1-(6-methoxy-1,2,3,4-tetrahydronaphthalen-2-ylacetyl)-L-proline was prepared by hydrolyzing 1-(6-methoxy-1,2,3,4-tetrahydronaphthalen-2-ylacetyl)-L-proline methyl ester which was prepared in Reference Example 20 (yield: 89%).
mp 144°–149° C.
IR(KBr) cm$^{-1}$: 2825–3000, 1700, 1685, 1230
NMR(CDCl$_3$) δ: 1.22–2.96(13H, m), 3.37–3.89(5H, m), 4.33–4.70(1H, m), 6.56–6.74(2H, m), 6.89–7.03(1H, m)

Reference Example 22

A colorless oil of 3-(6-methoxy-1,2,3,4-tetrahydronaphthalen-2-ylacetyl)-L-thioproline ethyl ester was prepared in the same manner as Reference Example 1, except that 6-methoxy-1,2,3,4-tetrahydronaphthalen-2-ylacetic acid was used instead of 2-indanylacetic acid (yield: 80%).
IR(neat) cm$^{-1}$: 2910, 1740, 1650, 1500, 1400, 750
NMR(CDCl$_3$) δ: 1.25–1.55(4H, m), 1.98–3.38(10H, m), 3.77(3H, s), 4.18–5.17(5H, m), 6.61–6.69(2H, m), 6.93–6.99(1H, m)

Reference Example 23

In the same manner as in Reference Example 2, colorless crystals of 3-(6-methoxy-1,2,3,4-tetrahydronaphthalen-2-ylacetyl)-L-thioproline were prepared by hydrolyzing 3-(6-methoxy-1,2,3,4-tetrahydronaphthalen-2-ylacetyl)-L-thioproline ethyl ester which was prepared in Reference Example 22 (yield: 83%).
mp 170°–180° C.
IR(KBr) cm$^{-1}$: 2925, 2550, 1710, 1600, 1450, 1430, 800, 720
NMR(CDCl$_3$) δ: 1.40–3.40(11H, m), 3.78(3H, s), 4.50–5.15(3H, m), 6.61–6.68(2H, m), 6.94–6.98(1H, m)

Reference Example 24

3-(5,7-dimethyl-1,2,3,4-tetrahydronaphthalen-2-ylacetyl)-L-thioproline ethyl ester

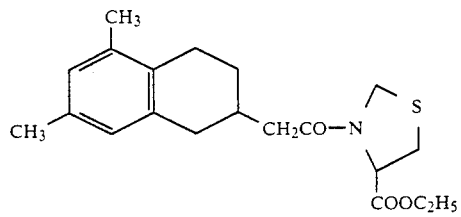

A colorless oil of 3-(5,7-dimethyl-1,2,3,4-tetrahydronaphthalen-2-ylacetyl)-L-thioproline ethyl ester was prepared in the same manner as Reference Example 1, except that 5,7-dimethyl-1,2,3,4-tetrahydronaphthalen-2-ylacetic acid was used instead of 2-indanylacetic acid (yield: 51%).
IR(neat) cm$^{-1}$: 2900, 1735, 1650, 1400
NMR (CDCl$_3$) δ: 1.25–1.36(3H, m), 1.43–1.61(1H, m), 1.96–3.00(14H, m), 3.18–3.39(2H, m), 4.18–4.29(2H, m), 4.50–5.19(3H, m), 6.75(1H, s), 6.85(1H, s)

Reference Example 25

In the same manner as in Reference Example 2, a colorless viscous oil of 3-(5,7-dimethyl-1,2,3,4-tetrahydronaphthalene-2-ylacetyl)-L-thioproline was prepared by hydrolyzing 3-(5,7-dimethyl-1,2,3,4-tetrahydronaphthalen-2-ylacetyl)-L-thioproline ethyl ester which was prepared in Reference Example 24 (yield: 75%).
IR(neat) cm$^{-1}$: 2900, 1730, 1610, 1420
NMR(CDCl$_3$) δ: 1.39–1.61(1H, m), 1.96–2.96(14H, m), 3.18–3.39(2H, m), 4.50–4.64(2H, m), 4.79–5.15(1H, m), 6.45(1H, brs), 6.73(1H, s), 6.82(1H, s)

Reference Example 26

Colorless crystals of 3-(2-indanylacetyl)-D-thioproline were prepared in the same manner as in Reference Example 10, except that D-thioproline was used instead of L-piperidin-2-ylcarboxylic acid (yield: 52%).
mp 111°–113° C.
IR(KBr) cm$^{-1}$: 2800, 2550, 1720, 1600, 1460, 745
NMR(CDCl$_3$) δ: 2.45–3.39(9H, m), 4.49–5.14(3H, m), 7.09–7.24(4H, m), 9.58(1H, s)

Reference Example 27

Colorless crystals of 1-[(S)-(−)-1,2,3,4-tetrahydronaphthalen-2-ylacetyl]-L-proline methyl ester were prepared in the same manner as in Reference Example 1, except that (S)-(−)-1,2,3,4-tetrahydronaphthalen-2-ylacetic acid and L-proline methyl ester were used instead of 2-indanyl acetic acid and L-thioproline ethyl ester, respectively yield: 72%).
mp 62°–64° C.
[α]$_D$ −132.4° (c=1.01, MeOH)
IR(KBr) cm$^{-1}$: 2830–3070, 1755, 1640, 1430, 1170, 750
NMR(CDCl$_3$) δ: 1.45–1.52(1H, m), 1.91–2.56(9H, m), 2.78–3.00(3H, m), 3.46–3.68(2H, m), 3.74(3H, s), 4.52(1H, dd, J=4 Hz, 8.5 Hz), 7.01–7.12(4H, m)

Reference Example 28

In the same manner as in Reference Example 2, colorless crystals of 1-[(S)-(−)-1,2,3,4-tetrahydronaphthalen-2-ylacetyl]-L-proline were prepared by hydrolyzing 1-[(S)-(−)-1,2,3,4-tetrahydronaphthalen-2-ylacetyl]-L-proline methyl ester which was prepared in Reference Example 27 (yield: 98%).
mp 129°–130° C.
[α]$_D$ −111.8° (c=1.00, MeOH)
IR(KBr) cm$^{-1}$: 2470–3070, 1730, 1590, 1175, 750
NMR(CDCl$_3$) δ: 1.43–1.57(1H, m), 1.95–2.57(9H, m), 2.79–3.00(3H, m), 3.42–3.62(2H, m), 4.61–4.67(1H, m), 7.01–7.13(4H, m), 6.75–8.05(1H, br)

Reference Example 29

A colorless oil of 1-[(R)-(+)-1,2,3,4-tetrahydronaphthalen-2-ylacetyl]-L-proline methyl ester was prepared in the same manner as in Reference Example 1, except that (R)-(+)-1,2,3,4-tetrahydronaphthalen-2-ylacetic acid and L-proline methyl ester were used instead of 2-indanyl acetic acid and L-thioproline ethyl ester, respectively (yield: 86%).
[α]$_D$ −8.3° (c=1.07, MeOH)
IR(neat) cm$^{-1}$: 2840–3060, 1740, 1640, 1170, 745
NMR(CDCl$_3$) δ: 1.42–1.52(1H, m), 1.92–2.58(9H, m), 2.79–3.01(3H, m), 3.47–3.68(2H, m), 3.74(3H, s), 4.52(1H, dd, J=4 Hz, 8.5 Hz), 7.04–7.12(4H, m)

Reference Example 30

In the same manner as in Reference Example 2, colorless crystals of 1-[(R)-(+)-1,2,3,4-tetrahydronaphthalen-2-(ylacetyl]-L-proline were prepared by hydrolyzing 1-[(R)-(+)-1,2,3,4-tetrahydronaphthalen-2-ylacetyl]-L-proline methyl ester which was prepared in Reference Example 29 (yield: 66%).

mp 153°–154° C.
$[\alpha]_D$ −0.2° (c=0.95, MeOH)
IR(KBr) cm$^{-1}$: 2500–3200, 1750, 1610, 1450, 765
NMR(CDCl$_3$) δ: 1.42–1.57(1H, m), 1.96–2.57(9H, m), 2.79–3.00(3H, m), 3.43–3.59(2H, m), 4.59–4.64(1H, m), 7.01–7.13(4H, m), 8.95–9.25(1H, br)

Reference Example 31

Colorless crystals of 3-[(S)-(−)-1,2,3,4-tetrahydronaphthalen-2-ylacetyl]-D-thioproline ethyl ester were prepared in the same manner as in Reference Example 1, except that (S)-(−)-1,2,3,4-tetrahydronaphthalen-2-ylacetic acid and D-thioproline ethyl ester were used instead of 2-indanyl acetic acid and L-thioproline ethyl ester, respectively (yield: 83%).

mp 81°–83° C.
$[\alpha]_D$ +39.7° (c=1.01MeOH)
IR(KBr) cm$^{-1}$: 2825–3000, 1735, 1645, 1405
NMR(CDCl$_3$) δ:1.21–3.36(14H, m), 4.14–4.29(2H, m), 4.46–5.14(3H, m), 6.96–7.11(4H, m)

Reference Example 32

In the same manner as in Reference Example 2, colorless crystals of 3-[(S)-(−)-1,2,3,4-tetrahydronaphthalen-2-ylacetyl]-D-thioproline were prepared by hydrolyzing 3-[(S)-(−)-1,2,3,4-tetrahydronaphthalen-2-ylacetyl]-D-thioproline ethyl ester which was prepared in Reference Example 31 (yield: 75%).

mp 145°–149° C.
$[\alpha]_D$ +34.2° (c=0.93, MeOH)
IR[KBr] cm$^{-1}$: 2300–3250, 1705, 1600, 1420, 745
NMR(CDCl$_3$) δ: 1.32–1.54(1H, m), 1.86–2.04(1H, m), 2.25–3.36(9H, m), 4.43–5.18(3H, m), 6.93–7.11(4H, m), 10.88(1H, s)

Reference Example 33

Colorless crystals of 3-[(R)-(+)-1,2,3,4-tetrahydronaphthalen-2-ylacetyl]-L-thioproline ethyl ester were prepared in the same manner as in Reference Example 1, except that (R)-(+)-1,2,3,4-tetrahydronaphthalen-2-ylacetic acid was used instead of 2-indanyl acetic acid (yield: 65%).

mp 78°–80° C.
$[\alpha]_D$ −41.7° (c=1.09, MeOH)
IR(KBr) cm$^{-1}$: 2840–3050, 1740, 1650, 1410, 750
NMR(CDCl$_3$) δ: 1.21–1.57(4H, m), 1.93–3.37(11H, m), 4.16–5.18(5H, m), 6.98–7.14(4H, m)

Reference Example 34

In the same manner as in Reference Example 2, colorless crystals of 3-[(R)-(+)-1,2,3,4-tetrahydronaphthalen-2-ylacetyl]-L-thioproline were prepared by hydrolyzing 3-[(R)-(+)-1,2,3,4-tetrahydronaphthalen-2-ylacetyl]-L-thioproline ethyl ester which was prepared in Reference Example 33 (yield: 50%).

mp 151°–152° C.
$[\alpha]_D$ −32.6° (c=0.68m MeOH)
IR(KBr) cm$^{-1}$: 2900, 2550, 1700, 1600, 1420, 740
NMR(CDCl$_3$) δ: 1.44–1.59(1H, m), 1.99–2.05(1H, m), 2.35–3.36(9H, m), 4.50–5.12(4H, m), 7.03–7.12(4H, m)

Example 1

3-[3-(2-indanylacetyl)-L-thioprolyl]thiazolidine

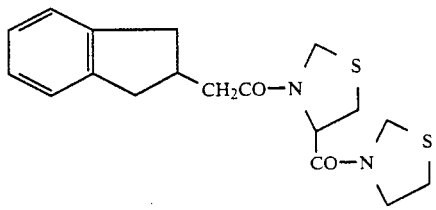

0.60 g of 3-(2-indanylacetyl)-L-thioproline was suspended in 5 ml of methylene chloride. To the suspension was added 0.46 g of WSC HCl with stirring at room temperature. After 5 minutes, 0.18 g of thiazolidine dissolved in 5 ml of methylene chloride was added to the mixture, and the mixture was stirred for 17 hours at room temperature. The reaction mixture was washed with water, diluted hydrochloric acid, and saturated sodium hydrogen carbonate in this order. The organic layer was dried over anhydrous magnesium sulfate, and the solvent was evaporated under reduced pressure. The residue thus obtained was purified by silica gel column chromatography to produce 0.40 g of 3-[3-(2-indanylacetyl)-L-thioprolyl]thiazolidine as a colorless oil (yield: 55%).

The colorless oil resulted was treated with isopropyl ether to obtain colorless crystals.

mp 78°–81.5° C.
IR(neat) cm$^{-1}$: 2925, 1640, 1405, 740
NMR(CDCl$_3$) δ: 2.13–3.40(13H, m), 4.50(4H, s), 4.87–5.17(1H, m), 7.03(4H, s)

Example 2

Colorless crystals of 1-[3-(2-indanylacetyl)-L-thioprolyl]pyrrolidine were prepared in the same manner as in Example 1, except that pyrrolidine was used instead of thiazolidine (yield: 70%).

mp 82°–83° C.
IR(KBr) cm$^{-1}$: 2830–3070, 1640, 1420, 750
NMR(CDCl$_3$) δ: 1.79–2.09(4H, m), 2.54–2.70(4H, m), 2.90–3.89(11H, m), 4.64(2H, dd, J=9 Hz), 5.08(1H, t, J=7 Hz), 7.10–7.20(4H, m)

Example 3

A colorless oil of 3-[1-(2-indanylacetyl)-L-prolyl]-thiazolidine was prepared in the same manner as in Example 1, except that 1-(2-indanylacetyl)-L-proline was used instead of 3-(2-indanylacetyl)-L-thioproline (yield: 69%).

IR(neat) cm$^{-1}$: 2830–3070, 1640, 1420, 1180, 740
NMR(CDCl$_3$) δ: 1.54–4.14(17H, m), 4.3–4.92(1H, m), 4.52(2H, s), 7.02(4H, s)

Example 4

A colorless oil of 1-[1-(2-indanylacetyl)-L-prolyl]pyrrolidine was prepared in the same manner as in Example 1, except that 1-(2-indanylacetyl)-L-proline and pyrrolidine were used instead of 3-(2-indanylacetyl)-L-thioproline and thiazolidine, respectively (yield: 62%).

IR(neat) cm$^{-1}$: 2880–3080, 1640, 1430, 1320, 745
NMR(CDCl$_3$) δ: 1 35–3.98(21H, m), 4.47–4.84(1H, m), 7.08(4H, s)

Example 5

A colorless oil of 3-[4-(2-indanylacetyl)-DL-1,4-thiazan-3-ylcarbonyl]thiazolidine was prepared in the same manner as in Example 1, except that 4-(2-indanylacetyl)-DL-1,4-thiazan-3-ylcarboxylic acid was used instead of 3-(2-indanylacetyl)-L-thioproline (yield: 84%).

IR(neat) cm$^{-1}$: 2972, 1643, 1433, 1340, 1225, 1190
NMR(CDCl$_3$) δ: 2.40–3.27(13H, m), 3.60–4.06(4H, m), 4.60(2H, s), 5.40–5.56(1H, m), 7.09–7.25(4H, m)

Example 6

A colorless oil of 1-[4-(2-indanylacetyl)-DL-1,4-thiazan-3-ylcarbonyl]pyrrolidine was prepared in the same manner as in Example 1, except that 4-(2-indanylacetyl)-DL-1,4-thiazan-3-ylcarboxylic acid and pyrrolidine were used instead of 3-(2-indanylacetyl)-L-thioproline and thiazolidine, respectively (yield: 62%).

IR(neat) cm$^{-1}$: 2930, 1643, 1418, 1300, 1285, 1260, 1182, 1022
NMR(CDCl$_3$) δ: 1.72–2.05(4H, m), 2.40–3.27(11H, m), 3.27–3.72(4H, m), 3.84–4.06(2H, m), 5.37–5.49(1H, m), 7.04–7.21(4H, m)

Example 7

A colorless oil of 3-[1-(2-indanylacetyl)-DL-piperidin-2-ylcarbonyl]thiazolidine was prepared in the same manner as in Example 1, except that 1-(2-indanylacetyl)-DL-piperidin-2-ylcarboxylic acid was used instead of 3-(2-indanylacetyl)-L-thioproline (yield: 71%).

IR(neat) cm$^{-1}$: 2925, 1630, 1420, 740
NMR(CDCl$_3$) δ: 1.61–1.99(6H, m), 2.52–2.67(4H, m), 2.85–3.23(5H, m), 3.56–3.92(4H, m), 4.51–4.64(2H, m), 5.37(1H, brs), 7.10–7.25(4H, m)

Example 8

A colorless oil of 1-[1-(2-indanylacetyl)-DL-piperidin-2-ylcarbonyl]pyrrolidine was prepared in the same manner as in Example 1, except that 1-(2-indanylacetyl)-DL-piperidin-2-ylcarboxylic acid and pyrrolidine were used instead of 3-(2-indanylacetyl)-L-thioproline and thiazolidine, respectively (yield: 68%).

IR(neat) cm$^{-1}$: 2950, 2870, 1640, 1420, 750
NMR(CDCl$_3$) δ: 1.61–1.97(10H, m), 2.52–2.68(4H, m), 2.88–2.99(1H, m), 3.11–3.24(2H, m), 3.35–3.75(6H, m), 5.33–5.35(1H, m), 7.1–7.21(4H, m)

Example 9

A colorless oil of 3-[1-(2-indanylacetyl)-L-piperidine-2-ylcarbonyl]thiazolidine was prepared in the same manner as in Example 1, except that 1-(2-indanylacetyl)-L-piperidine-2-ylcarboxylic acid was used instead of 3-(2-indanylacetyl)-L-thioproline (yield: 72%).

IR(neat) cm$^{-1}$: 2910, 1630, 1410, 740
NMR(CDCl$_3$) δ: 1.60–1.99(6H, m), 2.52–2.67(4H, m), 2.85–3.23(5H, m), 3.60–3.83(4H, m), 4.54–4.64(2H, m), 5.37(1H, brs), 7.11–7.21(4H, m)

Example 10

A colorless oil of 1-[1-(2-indanylacetyl)-L-piperidine-2ylcarbonyl]pyrrolidine was prepared in the same manner as in Example 1, except that 1-(2-indanylacetyl)-L-piperidine-2ylcarboxylic acid and pyrrolidine were used instead of 3-(2-indanylacetyl)-L-thioproline and thiazolidine, respectively (yield: 48%).

IR(neat) cm$^{-1}$: 2940, 2850, 1620, 1420, 730
NMR(CDCl$_3$) δ: 1.60–2.01(10H, m), 2.51–2.68(4H, m), 2.88–2.99(1H, m), 3.11–3.23(2H, m), 3.34–3.79(6H, m), 5.32–5.35(1H, m), 7.10–7.20(4H, m)

Example 11

A colorless oil of 1-[1-(2-indanylacetyl)-D-piperidine-2-ylcarbonyl]pyrrolidine was prepared in the same manner as in Example 1, except that 1-(2-indanylacetyl)-D-piperidine-2ylcarboxylic acid and pyrrolidine were used instead of 3-(2-indanylacetyl)-L-thioproline and thiazolidine, respectively (yield: 91%).

IR(neat) cm$^{-1}$: 2930, 2850, 1630, 1420, 730
NMR(CDCl$_3$) δ: 1.60–1.99(10H, m), 2.52–2.68(4H, m), 2.88–2.99(1H, m), 3.11–3.23(2H, m), 3.35–3.79(6H, m), 5.32–5.35(1H, m), 7.10–7.20(4H, m)

Example 12

3-[1-(1,2,3,4-tetrahydronaphthalen-2-ylcarbonyl)-L-prolyl]thiazolidine

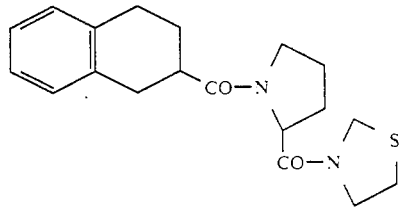

A colorless oil of 3-[1-(1,2,3,4-tetrahydronaphthalene-2ylcarbonyl)-L-prolyl]thiazolidine was prepared in the same manner as in Example 1, except that 1-(1,2,3,4-tetrahydronaphthalen-2-ylcarbonyl)-L-proline was used instead of 3-(2-indanylacetyl)-L-throproline (yield: 61%).

IR(neat) cm$^{-1}$: 2880–3070, 1650, 1430, 1360, 1340, 1325, 750
NMR(CDCl$_3$) δ: 1.49–2.40(6H, m), 2.58–3.22(7H, m), 3.32–4.07(4H, m), 4.31–4.78(3H, m), 6.92(4H, s)

Example 13

A colorless oil of 1-[1-(1,2,3,4-tetrahydronaphthalene-2-ylcarbonyl)-L-prolyl]pyrrolidine was prepared in the same manner as in Example 1, except that 1-(1,2,3,4-tetrahydronaphthalen-2ylcarbonyl)-L-proline and pyrrolidine were used instead of 3-(2-indanylacetyl)-L-thioproline and thiazolidine, respectively (yield: 52%).

IR(neat) cm$^{-1}$: 2880–3070, 1640, 1435, 1360, 750
NMR(CDCl$_3$) δ: 1.48–2.27(10H, m), 2.60–3.02(5H, m), 3.13–3.89(6H, m), 4.37–4.73(1H, m), 6.88(4H, s)

Example 14

A colorless oil of 3-[1(1,2,3,4-tetrahydronaphthalene-2ylacetyl)-L-prolyl]thiazolidine was prepared in the same manner as in Example 1, except that 1-(1,2,3,4-tetrahydronaphthalen-2-ylacetyl)-L-proline was used instead of 3-(2-indanylacetyl)-L-thioproline (yield: 33%).

IR(neat) cm$^{-1}$: 2920, 1630, 1420, 740
NMR(CDCl$_3$) δ: 1.40–1.55(1H, m), 1.92–3.17(14H, m), 3.48–4.20(4H, m), 4.50–4.87(3H, m), 7.07(4H, s)

Example 15

3-[3-(2-indanylacetyl)-L-thioprolyl]-L-thioproline ethyl ester

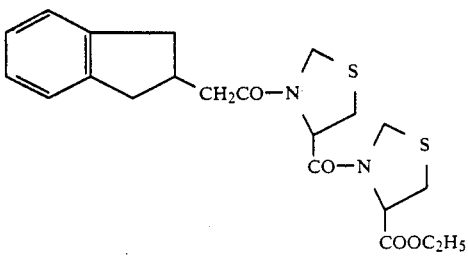

A colorless oil of 3-[3-(2-indanylacetyl)-L-thioprolyl]-L-thioproline ethyl ester was prepared in the same manner as in Example 1, except that L-thioproline ethyl ester was used instead of thiazolidine (yield: 75%).

IR(neat) $cm^{-1}$: 2940, 1740, 1650, 1400, 740
NMR(CDCl$_3$) δ: 1.29(3H, t, J=7 Hz), 2.50-3.41(11H, m), 4.21(2H, q, J=7 Hz), 4.57-4.70(3H, m), 5.00-5.20(3H, m), 7.10614 7.26(4H, m)

Example 16

1-[1-(2-indanylacetyl-L-prolyl]-L-proline methyl ester

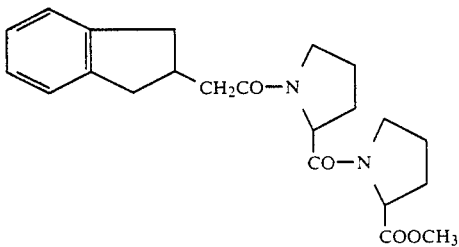

Into a 4 ml of tetrahydrofuran were dissolved 0.82 g of 1-(2-indanylacetyl)-L-proline and 0.35 g of N-hydroxysuccinimide. To the solution was dropwise added a solution of 0.74 g of DCC in 2 ml of tetrahydrofuran at room temperature with stirring. After stirring for a further 17 hours at the same temperature, insoluble components were removed by filtration. From the filtrate the solvent was evaporated under reduced pressure. The oily residue thus obtained was washed with n-hexane, dissolved in 5 ml of benzene, and treated with activated carbon. Benzene was evaporated under reduced pressure to produce 0.72 g of 1-(2-indanylacetyl)-L-prolyloxysuccinimide as coloress amorphous solid.

2.6 g of active ester prepared above and 1.2 g of L-proline methyl ester hydrochloride were suspended in 10 ml of tetrahydrofuran. To the suspension was added 0.7 g of triethylamine and the mixture was stirred for 17 hours at room temperature. The solvent was evaporated from the reaciton mixture. The residue was dissolved in ethyl acetate and washed with water, diluted hydrochloric acid, and saturate sodium hydrogen carbonate in this order. The organic layer was dried over anhydrous magnesium sulfate. After evaporating the solvent under reduced pressure, the residue was purified by silica gel column chromatography to obtain 1.0 g of 1-[1-(2-indanylacetyl)-L-prolyl]-L-proline methyl ester as an oil. (yield: 37%)

IR(neat) $cm^{-1}$: 2950, 1740, 1630, 1430, 740
NMR(CDCl$_3$) δ: 1.94-3.90(22H, m), 4.57-4.73(2H, m), 7.09-7.19(4H, m)

Example 17

Coloress crystals of 1-[1-(2-indanylacetyl)-L-prolyl]-L-proline were prepared in the same manner as in Reference Example 2, except that 1-[1-(2-indanylacetyl)-L-prolyl]-L-proline methyl ester prepared in Example 16 was used instead of 3-(2-indanylacetyl)-L-thioproline ethyl ester (yield: 27%).

mp 163°-165° C.
IR(KBr) $cm^{-1}$: 2950, 1720, 1655, 1600, 1430, 740
NMR(CDCl$_3$) δ: 1.95-3.68(19H, m), 4.10-5.15(3H, m), 7.10-7.20(4H, m)

Example 18

3-[1-(2-indenylacetyl)-L-prolyl]thiazolidine

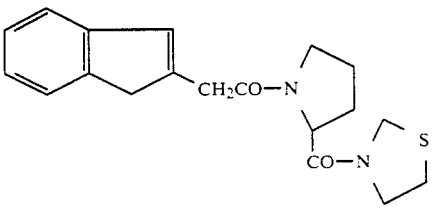

A pale yellow amorphous solid of 3-[1-(6b 2-indenylacetyl)-L-prolyl]thiazolidine was prepared in the same manner as in Example 1, except that 1-(2-indenylacetyl)-L-proline was used instead of 3-(2-indanylacetyl)-L-thioproline (yield: 55%).

IR(KBr) $cm^{-1}$: 2880-3060, 1640, 1420, 1320, 755, 720
NMR(CDCl$_3$) δ:1.93-2.25(4H, m), 2.96-3.17(2H, m), 3.45(2H, s), 3.56(2H, s), 3.49-4.22(4H, m), 4.49-4.88(3H, m), 6.70(1H, s), 7.09-7.40(4H, m)

Example 19

A pale yellow amorphous solid of 1-[1-(2-indenylacetyl)-L-prolyl]pyrrolidine was prepared in the same manner as in Example 1, except that 1-(2-indenylacetyl)-L-proline and pyrrolidine were used instead of 3-(2-indanylacetyl)-L-thioproline and thiazolidine, respectively (yield: 62%).

IR(KBr) $cm^{-1}$: 2880-3050, 1635, 1430, 1335, 1200, 750, 715
NMR(CDCl$_3$) δ: 1.81-2.27(8H, m), 3.46(2H, s), 3.56(2H, s), 3.34-3.86(6H, m), 4.62-4.71(1H, m), 6.70(1H, 2), 7.08-7.39(4H, m)

Example 20

1-[1-(2-indanylacetyl)-L-prolyl]-L-prolinol

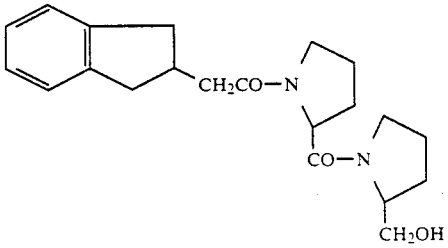

0.57 g of sodium boron hydride was added with stirring to 9 ml of a 80% methanol solution under ice-cooling. To the mixture was added dropwise 1.15 g of 1-[1-

(2-indanylacetyl)-L-prolyl]-L-proline methyl ester dissolved in a mixed solution of 5 ml of tetrahydrofuran and 5 ml of methanol. After addition, the mixture was stirred for 15 hours at room temperature. The reaction mixture was acidified by adding diluted hydrochloric acid and extracted with ether. The organic layer obtained was washed with brine and dried over anhydrous sodium sulfate. After evaporating the solvent under reduced pressure, the residue was purified by silica gel column chromatography to obtain 0.73 g of 1-[1-(2-indanylacetyl)-L-prolyl]-L-prolinol as an oily substance. (yield: 68%)

IR(neat) cm$^{-1}$: 3410, 2850-2970, 1635, 1440, 745

NMR(CDCl$_3$) δ: 1.53-2.23(8H, m), 2.40-2.72(4H, m) 2.92-3.00(1H, m), 3.10-3.22(2H, m), 3.45-3.98(6H, m), 4.10-5.18(2H, m), 5.20(1H, brs), 7.06-7.22(4H, m)

Example 21

1-[1-(2-indanylacetyl)-L-prolinal

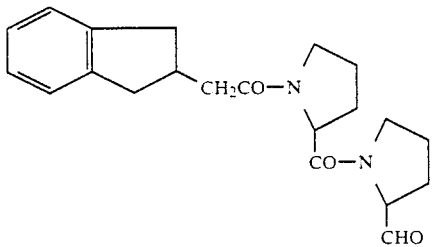

0.94 g of oxalyl chloride was dissolved in 9.5 ml of methylene chloride. To the mixture which was stirred at −60° C. was dropwise added 0.69 g of dimethylsulfoxide dissolved in 1.8 ml of methylene chloride. After stirring for 10 minutes, 1.30 g of 1-[1-(2-indanylacetyl)-L-prolyl]-L-prolinol prepared in Example 20 dissolved in 9.5 ml of methylene chloride was slowly added dropwise to the mixture. After 15 minutes, 2.24 g of triethylamine was added, and stirred at −30° C. for 1 hour. The solution was left until its temperature became the room temperature, and then water ws added the mixture was stirred. The organic layer obtained was washed with diluted hydrochloric acid, saturated sodium hydrogen carbonate, and water in this order and dried over anhydrous sodium sulfate. After evaporating the solvent under reduced pressure, the residue was purified by silica gel column chromatography to obtain 0.80 g of 1-]1-(2-indanylacetyl)-L-prolyl]-L-prolinal as colorless oil (yield: 62%)

IR(neat) cm$^{-1}$: 2850-3070, 1735, 1640, 1435, 750

NMR(CDCl$_3$) δ: 1.74-2.25(8H, m), 2.37-2.71(4H, m), 2.94-3.24(3H, m), 3.44-3.95(4H, m), 4.60-4.74(2H, m), 7.1--7.21(4H, m), 9.54(1H, d, J=2 Hz)

Example 22

3-[3-(1,2,3,4-tetrahydronaphthalen-2ylacetyl)-L-thioprolyl]thiazolidine

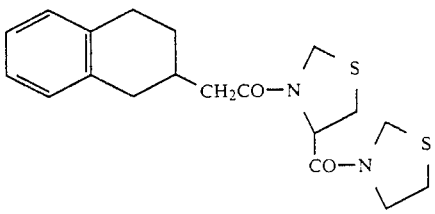

4.6 g of 3-(1,2,3,4-tetrahydronaphthalen-2-ylacetyl)-L-thioproline and 13.5 g of WSC HCl were added to 40 ml of methylene chloride and the mixture was stirred at room temperature for 5 minutes. To the mixture was added 1.3 g of thiazolidine dissolved in 40 ml of methylene chloride solution and the mixture was stirred for 17 hours at room temperature. The reaction mixture was washed with water, diluted hydrochloric acid, and saturated sodium hydrogen carbonate in this order. The organic layer was dried over anhydrous magnesium sulfate, and the solvent was evaporated under reduced pressure. The residue thus obtained was purified by silica gel column chromatography to produce 2.8 g of 3-[3-(1,2,3,4-tetrahydronaphthalen-2-ylacetyl)-L-thioprolyl]thiazolidine as colorless powder (yield: 49%).

mp 80°-96° C.

IR(KBr) cm$^{-1}$: 2920, 1635, 1430, 1400, 750

NMR(CDCl$_3$) δ: 1.41-3.40(13H, m), 3.60-5.25(7H, m), 6.80-7.36(4H, m)

Example 23

Colorless crystals of 1-[3-(1,2,3,4-tetrahydronaphthalen-2-ylacetyl)-L-thioprolyl]pyrrolidine were prepared in the same manner as in Example 1, except that 3-(1,2,3,4-tetrahydronaphthalen-2-ylacetyl)-L-thioproline and pyrrolidine were used instead of 3-(2-indanylacetyl)-L-thioproline and thiazolidine, respectively (yield: 52%).

mp 118°-129° C.

IR(KBr) cm$^{-1}$: 2920, 1635, 1435, 1400, 745

NMR(CDCl$_3$) δ: 1.42-1.53(1H, m), 1.83-2.08(5H, m), 2.30-2.60(4H, m), 2.77-3.66(9H, m), 4.65-4.75(2H, m), 5.10(1H, t, J=7 Hz), 7.02-7.11(4H, m)

Example 24

Colorless crystals of 1-[1-(1,2,3,4-tetrahydronaph-thalen-2-ylacetyl)-L-prolyl]pyrrolidine were prepared in the same manner as in Example 1, except that 1-(1,2,3,4-tetrahydronaphthalen-2-ylacetyl)-L-proline and pyrrolidine were used instead of 3-(2-indanylacetyl]-L-thioproline and thiazolidine, respectively (yield: 46%).

mp 110°-113° C.

IR(KBr) cm$^{-1}$: 2850-3070, 1635, 1440, 1420, 1320, 750

NMR(CDCl$_3$) δ: 1.40-2.54(14H, m), 2.74-2.98(3H, m), 3.34-3.88(6H, m), 4.66-4.71(1H, m), 6.98-7.07(4H, m)

Example 25

1-{3-[3-(indan-2-yl)propionyl]-L-thioprolyl}pyrrolidine

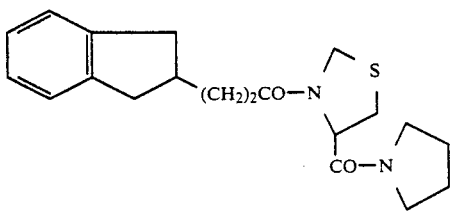

0.89 g of 1-L-thioprolylpyrrolidine hydrochloride was suspended in 20 ml of methylene chloride. To the suspension were added 0.40 g of triethylamine and 0.76 g of 3-(indan-2-yl)propionic acid under ice-cooling with stirring. After 10 minutes, 0.92 g of WSC.HCl was added to the mixture under ice-cooling while stirring. The mixture was sirred for 16 hours at room temperature. The reaction mixture was washed with diluted hydrochloric acid, water, and saturated sodium hydrogen carbonate in this order. The organic layer was dried over anhydrous magnesium sulfate, and the solvent was evaporated under reduced pressure. The residue thus obtained was recrystallized from ethyl acetate/isopropyl ether to produce 1.02 g of 1-{3-[3-(indan-2-yl)propionyl]-L-thioprolyl]pyrrolidine as colorless crystals (yield: 71%).

mp 92°–93° C.

IR(KBr) cm$^{-1}$: 2900, 1660, 1640, 1410, 750

NMR(CDCl$_3$) δ: 1.84–2.04(6H, m), 2.44–2.65(5H, m), 3.02–3.61(7H, m), 3.82–3.91(1H, m), 4.67–4.75(2H, m), 5.06(1H, t, J=7 Hz), 7.09–7.19(4H, m)

Example 26

Colorless crystals of 1-{3-[4-(indan-2-yl)butanoyl]-L-thioprolyl}pyrrolidine were prepared in the same manner as in Example 25, except that 4-(indan-2-yl)butyric acid was used instead of 3-(indan-2-yl)propionic acid (yield: 49%).

mp 99°–100° C.

IR(KBr) cm$^{-1}$: 2950, 1660, 1640, 1410, 750

NMR(CDCl$_3$) δ: 1.53–2.04(8H, m), 2.39–2.63(5H, m), 3.00–3.59(7H, m), 4.65–4.73(2H, m), 3.84–3.88(1H, m), 5.07(1H, t, J=7 Hz), 7.09–7.19(4H, m)

Example 27

1-[3-(5-chloroindan-2-ylacetyl)-L-thioprolyl]pyrrolidine

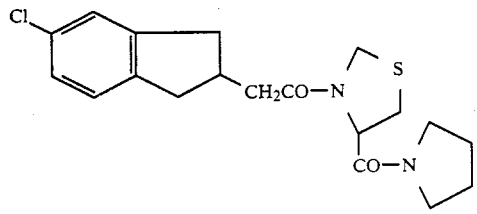

A colorless oil of 1-[3-(5-chloroindan-2-ylacetyl)-L-thioprolyl]pyrrolidine was prepared in the same manner as in Example 25, except that 5-chloroindan-2-ylacetic acid was used instead of 3-(indan-2-yl)propionic acid (yield: 93%).

IR(neat) cm$^{-1}$: 2950, 1640, 1420, 750

NMR(CDCl$_3$) δ: 1.82–2.68(8H, m), 2.91–3.89(9H, m), 4.58–5.12(3H, m), 7.06–7.17(3H, m)

Example 28

Colorless crystals of 1-[3-(5-methylindan-2-ylacetyl)-L-thioprolyl]pyrrolidine were prepared in the same manner as in Example 25, except that 5-methylindan-2-ylacetic acid was used instead of 3-(indan-2-yl)propionic acid (yield: 74%).

mp 115°–123° C.

IR(KBr) cm$^{-1}$: 2970, 1630, 1440, 1410, 805, 780

NMR(CDCl$_3$) δ: 1.81–2.23(4H, m), 2.30(3H, s), 2.33–3.90(13H, m), 4.53–5.13(3H, m), 6.92–7.09(3H, m)

Example 29

1-[3-(5-nitroindan-2-ylacetyl)-L-thioprolyl]pyrrolidine was prepared as a slightly yellow amorphous in the same manner as in Example 25, except that 5-nitroindane-2-yl)acetic acid was used instead of 3-(indan-2-yl)propionic acid (yield: 37%).

IR(neat) cm$^1$: 2960, 1655, 1630, 1410, 735

NMR(CDCl$_3$) δ: 1.78–2.09(4H, m), 2.57–2.62(2H, m), 2.65–2.79(2H, m), 2.98–3.33(5H, m), 3.35–3.48(2H, m), 3.53–3.60(1H, m), 3.73–3.86(1H, m), 4.61–4.72(2H, m), 5.09(1H, t, J=7 Hz), 7.30–7.33(1H, m), 8.01–8.04(2H, m)

Example 30

0.63 g of 1-[3-(5-nitroindan-2-ylacetyl)-L-thioprolyl]pyrrolidine prepared in Example 29 was dissolved in a mixed solution of 9 ml of acetic acid and 6 ml of water. 1.00 g of iron powder was gradually added with stirring. After 1 hour, the iron powder was filtered. The filtrate was alkalinized using 10% sodium hydroxide and extracted with ethyl acetate. The organic layer was washed with brine and dried over anhydrous magnesium sulfate. After evaporating the solvent, the residue obtained was purified by silica gel chromatography to produce 0.34 g of 1-[3-(5-aminoindan-2-ylacetyl)-L-thioprolyl]pyrrolidine as a brownish and oily substance (yield: 59%).

IR(neat) cm$^{-1}$: 3345, 2925, 1640, 1410, 750

NMR(CDCl$_3$) δ: 1.84–2.02(4H, m), 2.47–2.60(4H, m), 2.89–3.18(4H, m), 3.25–3.32(1H, m), 3.42–3.48(2H, m), 3.53–3.63(1H, m), 3.67–4.20(2H, br), 3.81–3.90(1H, m), 4.65(2H, dd, J=15 Hz, 9 Hz), 5.09(1H, t, J=7 Hz), 6.47–6.67(2H, m), 6.94–6.97(1H, m)

Example 31

Colorless crystals of 1-[3-(2-indanylacetyl)-D-thioprolyl]pyrrolidine were prepared in the same manner as in Example 1, except that 3-(2-indanylacetyl)-D-thioproline prepared in Reference Example 26 and pyrrolidine were used instead of 3-(2-indanylacetyl)-L-thioproline and thiazolidine, respectively (yield: 44%).

mp 81°–83° C.

IR(KBr) cm$^{-1}$: 2950, 1640, 1420, 750

NMR(CDCl$_3$) δ: 1.80–2.70(8H, m), 2.91–3.90(9H, m), 4.60–5.13(3H, m), 7.10–7.22(4H, m)

Example 32

1-[1-(6-methoxy-1,2,3,4-tetrahydronaphthalen-2-ylacetyl)-L-prolyl]pyrrolidine

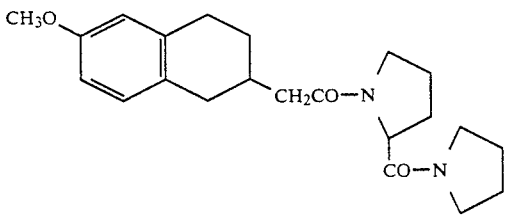

A colorless oil of 1-[1-(6-methoxy-1,2,3,4-tetrahydronaphthalen-2-ylacetyl)-L-prolyl]pyrrolidine was prepared in the same manner as in Example 1, except that 1-(6-methoxy-1,2,3,4-tetrahydronaphthalen-2-ylacetyl)-L-proline prepared in Reference Example 21 and pyrrolidine were used instead of 3-(2-indanylacetyl)-L-thioproline and thiazolidine, respectively (yield: 24%).

IR(neat) cm$^{-1}$: 2825-3050, 1655, 1635, 1430, 1035

NMR(CDCl$_3$) δ: 1.36-1.54(1H, m), 1.75-2.54(13H, m), 2.68-2.93(3H, m), 3.32-3.89(9H, m), 4.64-4.73(1H, m), 6.57-6.71(2H, m), 6.93-7.04(1H, m)

Example 33

A colorless oil of 3-[1-(6-methoxy-1,2,3,4-tetrahydronaphthalen-2-ylacetyl)-L-prolyl]thiazolidine was prepared in the same manner as in Example 1, except that 1-(6-methoxy-1,2,3,4-tetrahydronaphthalen-2-ylacetyl)-L-proline prepared in Reference Example 21 was used instead of 3-(2-indanylacetyl)-L-thioproline (yield: 57%).

IR(neat) cm$^{-1}$: 2825-2910, 1635, 1420, 1150

NMR(CDCl$_3$) δ: 1.36-1.57(1H, m), 1.86-2.54(10H, m), 2.68-4.25(11H, m), 4.46-4.89(3H, m), 6.57-6.71(2H, m), 6.93-7.04(1H, m)

Example 34

A colorless oil of 1-[3-(6-methoxy-1,2,3,4-tetrahydronaphthalen-2-ylacetyl)-L-thioprolyl]pyrrolidine was prepared in the same manner as in Example 1, except that 3-(6-methoxy-1,2,3,4-tetrahydronaphthalen-2-ylacetyl)-L-thioproline prepared in Reference Example 23 and pyrrolidine were used instead of 3-(2-indanylacetyl)-L-thioproline and thiazolidine, respectively (yield: 52%).

IR(neat) cm$^{-1}$: 2920, 1660, 1500, 1420, 750

NMR(CDCl$_3$) δ: 1.39-3.90(19H, m), 4.58-5.13(3H, m), 6.60-6.68(2H, m), 6.94-7.00(1H, m)

Example 35

A colorless oil of 3-[3-(6-methoxy-1,2,3,4-tetrahydronaphthalen-2-ylacetyl)-L-thioprolyl]thiazolidine was prepared in the same manner as in Example 1, except that 3-(6-methoxy-1,2,3,4-tetrahydronaphthalen-2-ylacetyl)-L-thioproline prepared in Reference Example 23 was used instead of 3-(2-indanylacetyl)-L-thioproline (yield: 67%).

IR(neat) cm$^{-1}$: 2925, 1640, 1500, 1420, 750

NMR(CDCl$_3$) δ: 1.42-3.49(13H, m), 3.70-5.17(10H, m), 6.60-6.69(2H, m), 6.87-7.00(1H, m)

Example 36

A colorless oil of 1-[3-(5,7-dimethyl-1,2,3,4-tetrahydronaphthalen-2-ylacetyl)-L-thioprolyl]pyrrolidine was prepared in the same manner as in Example 1, except that 3-(5,7-dimethyl-1,2,3,4-tetrahydronaphthalen-2-ylacetyl)-L-thioproline prepared in Reference Example 25 and pyrrolidine were used instead of 3-(2-indanylacetyl)-L-thioproline and thiazolidine, respectively (yield: 60%).

IR(neat) cm$^{-1}$: 2860-2960, 1640, 1410, 745

NMR(CDCl$_3$) δ: 1.39-1.57(1H, m), 1.79-3.93(24H, m), 4.54-4.75(2H, m), 5.10(1H, t, J=7 Hz), 6.71-6.82(2H, m)

Example 37

Colorless crystals of 1-[3-(2-indenylacetyl)-L-thioprolyl]pyrrolidine were prepared in the same manner as in Example 1, except that 3-(2-indenylacetyl)-L-thioproline prepared in Reference Example 19 and pyrrolidine were used instead of 3-(2-indanylacetyl)-L-thioproline and thiazolidine, respectively (yield: 44%).

mp 137°-137.5° C.

IR(KBr) cm$^{-1}$: 2950, 1655, 1635, 1445, 1400, 920

NMR(CDCl$_3$) δ: 1.86-2.04(4H, m), 3.12-3.89(10H, m), 4.72(2H, s), 5.05(1H, t, J=7 Hz), 6.72(1H, s), 7.13-7.41(4H, m)

Example 38

Colorless crystals of 3-[3-(2-indenylacetyl)-L-thioprolyl]thiazolidine were prepared in the same manner as in Example 1, except that 3-(2-indenylacetyl)-L-thioproline prepared in Reference Example 19 was used instead of 3-(2-indanylacetyl)-L-thioproline (yield: 36%).

mp 100°-101° C.

IR(KBr) cm$^{-1}$: 2950, 1640, 1415, 1170

NMR(CDCl$_3$) δ: 2.98-4.26(6H, m), 3.43(2H, s), 3.64(2H, s), 4.50-4.75(3H, m), 4.88-5.08(1H, m), 6.71(1H, s), 7.11-7.41(4H, m)

Example 39

1-[3-(2,3,4,5-tetrahydro-1H-benzocyclohepten-2-ylacetyl)-L-thioprolyl]pyrrolidine

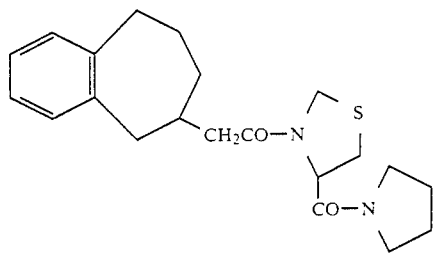

1-[3-(2,3,4,5-tetrahydro-1H-benzocyclohepten-2-ylacetyl)-L-thioprolyl]pyrrolidine was prepared as a colorless amorphous solid in the same manner as in Example 25, except that 2,3,4,5-tetrahydro-1H-benzocycloheptene-2-ylacetic acid was used instead of 3-(indan-2-yl)propionic acid (yield: 69%).

IR(KBr) cm$^{-1}$: 2900, 1635, 1405, 750

NMR(CDCl$_3$) δ: 1.65-2.34(9H, m), 2.77-2.88(4H, m), 3.10-3.88(6H, m), 4.41-4.61(2H, m), 5.03-5.12(1H, m), 7.08-7.26(4H, m)

Example 40

A colorless oil of 1-[1-(2-indenylacetyl)-L-prolyl]-L-proline methyl ester was prepared in the same manner as in Example 1, except that 1-(2-indenylacetyl)-L-proline and L-proline methyl ester were used instead of 3-(2-indanylacetyl)-L-thioproline and thiazolidine, respectively (yield: 75%).

IR(neat) cm$^{-1}$: 2950, 1745, 1640, 1430, 1195, 730

NMR(CDCl$_3$) δ: 1.85-2.31(8H, m), 3.44(2H, s), 3.55(2H, s), 3.71(3H, s), 3.36-3.97(4H, m), 4.51-4.77(2H, m), 6.68(1H, s), 7.08-7.39(4H, m)

Example 41

A colorless oil of 1-[1-(2-indenylacetyl)-L-prolyl]-L-prolyl]-L-prolinol was prepared in the same manner as in Example 20, except that 1-[1-(2-indenylacetyl)-L-prolyl]-L-proline methyl ester was used instead of 1-[1-(2-indanylacetyl)-L-proline methyl ester (yield: 58%).

IR(neat) cm-1 3400, 2970, 1630, 1440, 1050, 755

NMR(CDC13) 6: 1.50-2.28(8H, m), 3.44(2H, s), 3.56(2H, s), 3.30-3.81(6H, m), 4.06-4 39(1H, m) 4.60-4.89(1H, m) 5.04-5.22(1H,m), 6.71(1H, s), 7.09-7.39(4H, m)

Example 42

1-[1-(2-indenylacetyl)-L-prolyl]-L-prolinal

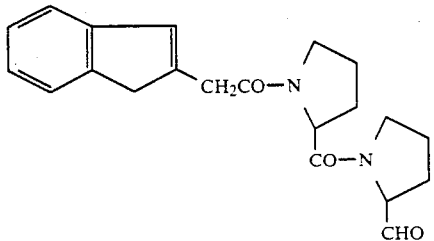

0.53 g of 1-[1-(2-indenylacetyl)-L-prolyl]-L-prolinol prepared in Preparation Example 41 and 0.76 g of triethylamine were dissoved in 6 ml of dimethylsulfoxide. To the solution was added 1.19 g of sulfur trioxide-pyridine complex and the mixture was stirred for one hour at room temperature. The reaction mixture to which 10 ml of ice-water was added was extracted with ethyl acetate. The organic layer was washed with diluted hydrochloric acid, water, and saturated sodium hydrogen carbonate in this order. The organic layer was dried over anhydrous magnesium sulfate and the solvent was evaporated under reduced pressure. The residue thus obtained was purified by silica gel chromatography to produce 0.29 g of 1-[1-(2-indenylacetyl)-L-prolyl]-L-prolinal as a colorless oil (yield: 55%).

IR(neat) cm$^{-1}$: 2700, 1725, 1635, 1430, 755

NMR(CDCl$_3$) δ: 1.65-2.32(8H, m), 3.39-4.00(8H, m), 4.55-4.77(2H, m), 6.69(1H, s), 7.03-7.44(4H, m), 9.53(1H, s)

Example 43

Colorless crystals of 1-{1-[(S)-(−)-1,2,3,4-tetrahydronaphthalen-2-ylacetyl]-L-prolyl}pyrrolidine were prepared in the same manner as in Example 1, except that 1-[(S)-(−)-1,2,3,4-tetrahydronaphthalen-2-ylacetyl]-L-proline prepared in Reference Example 28 and pyrrolidine were used instead of 3-(2-indanylacetyl)-L-thioproline and thiazolidine, respectively (yield: 52%).

mp 104°-106° C.

[α]$_D$ −83.8° (c=1.0, MeOH)

IR(KBr) cm$^{-1}$: 2830-3070, 1650, 1635, 1435, 750

NMR(CDCl$_3$) δ: 1.40-1.55(1H, m), 1.78-2.55(13H, m), 2.78-3.00(3H, m), 3.34-3.89(6H, m), 4.69(1H, dd, J=3.5 Hz, 8.5 Hz), 7.01-7.10(4H, m)

Example 44

Colorless crystals of 1-{1-[(R)-(+)-1,2,3,4-tetrahydronapthalen-2-ylacetyl]-L-prolyl}pyrrolidine were prepared in the same manner as in Example 1, except that 1-[(R)-(+)-1,2,3,4-tetrahydronaphthalene-2-ylacetyl]-L-proline prepared in Reference Example 30 and pyrrolidine were used instead of 3-(2-indanylacetyl)-L-thioproline and thiazolidine, respectively (yield: 44%).

mp 109°-110° C.

[α]$_D$ +13.7° (c=1.0, MeOH)

IR(KBr) cm$^{-1}$: 2830-2990, 1630, 1440, 1415, 750

NMR(CDCl$_3$) δ: 1.38-1.52(1H, m), 1.82-2.57(12H, m), 2.74-3.00(3H, m), 3.63-3.89(6H, m), 4.69(1H, dd, J=3.5 Hz, 8 Hz), 7.01-7.12(4H, m)

Example 45

A colorless oil of 3-{1-[(S)-(−)-1,2,3,4-tetrahydronaphthalen-2-ylacetyl]-L-prolyl}thiazolidine was prepared in the same manner as in Example 25, except that (S)-(−)-1,2,3,4-tetrahydronaphthalen-2-ylacetic acid and 3-L-prolylthiazolidine hydrochloride were used instead of 3-(indan-2-yl)propionic acid and 1-L-thioprolylpyrrolidine hydrochloride, respectively (yield: 63%).

[α]$_D$ −69.5° (c=1.01, MeOH)

IR(neat) cm$^{-1}$: 2910, 1640, 1420, 745

NMR(CDCl$_3$) δ: 1.44-1.51(1H, m), 1.95-2.53(9H, m), 2.80-3.17(5H, m), 3.48-4.20(4H, m), 4.50-4.87(3H, m), 7.02-7.09(4H, m)

Example 46

Colorless crystals of 3-{1-[(R)-(+)-1,2,3,4-tetrahydronaphthalen-2-ylacetyl]-L-prolyl}thiazolidine were prepared in the same manner as in Example 1, except that 1-[(R)-(+)-1,2,3,4-tetrahydronaphthalen-2-ylacetyl]-L-proline prepared in Reference Example 30 was used instead of 3-(2-indanylacetyl)-L-thioproline (yield: 30%).

mp 97°-99° C.

[α]$_D$ +19.5° (c=0.67, MeOH)

IR(KBr) cm$^{-1}$: 2840-3000, 1625, 1450, 1420

NMR(CDCl$_3$) δ: 1.36-1.54(1H, m), 1.86-3.21(14H, m), 3.46-4.25(4H, m), 4.46-4.86(3H, m), 7.04-7.10(4H, m)

Example 47

Colorless crystals of 1-{3-[(S)-(−)-1,2,3,4-tetrahydronaphthalen-2-ylacetyl]-L-thioprolyl}pyrrolidine were prepared in the same manner as in Example 25, except that (S)-(−)-1,2,3,4-tetrahydronaphthalen-2-ylacetic acid was used instead of 3-(indan-2-yl)propionic acid (yield: 81%).

mp 121°-122.5° C.

[α]$_D$ −153.1° (c=0.60, MeOH)

IR(KBr) cm$^{-1}$: 2085-3050, 1620, 1445, 1410

NMR(CDCl$_3$) δ: 1.41-1.59(1H, m), 1.79-3.64(17H, m), 3.79-3.93(1H, m), 4.67(1H, d, J=9 Hz), 4.72(1H, d, J=9 Hz), 5.12(1H, t, J=7 Hz), 7.00-7.13(4H, m)

Example 48

Colorless crystals of 1-{3-[(S)-(−)-1,2,3,4-tetrahydronaphthalen-2-ylacetyl]-D-thioprolyl}pyrrolidine were prepared in the same manner as in Example 1, except that 3-[(S)-(−)-1,2,3,4-tetrahydronaphthalen-2-ylacetyl]-D-thioproline prepared in Reference Example 32 and pyrrolidine were used instead of 3-(2-indanylacetyl)-L-thioproline and thiazolidine, respectively (yield: 65%).

mp 153°–155° C.

$[\alpha]_D$ +53.3° (c=1.01, MeOH)

IR(KBr) cm$^{-1}$: 2840–3000, 1635, 1440, 1400, 750

NMR(CDCl$_3$) δ: 1.43–1.61(1H, m), 1.79–3.93(17H, m), 4.57–4.79(2H, m), 5.11(1H, t, J=7 Hz), 7.04–7.14(4H, m)

Example 49

Colorless crystals of 1-{3-[(R)-(+)-1,2,3,4-tetrahydronaphthalen-2-ylacetyl]-L-thioprolyl}pyrrolidine were prepared in the same manner as in Example 1, except that 3-[(R)-(+)-1,2,3,4-tetrahydronaphthalen-2-ylacetyl]-L-thioproline prepared in Reference Example 34 and pyrrolidine were used instead of 3-(2-indanylacetyl)-L-thioproline and thiazolidine, respectively (yield: 31%).

mp 154°–156° C.

$[\alpha]_D$ −52.3° (c=0.85, MeOH)

IR(KBr) cm$^{-1}$: 2920, 1640, 1440, 1400, 750

NMR(CDCl$_3$) δ: 1.41–2.57(10H, m), 2.75–3.90(10H, m), 4.55–5.13(3H, m), 7.04–7.11(4H, m)

Example 50

Colorless crystals of 1-{3-[(R)-(+)-1,2,3,4-tetrahydronaphthalen-2-ylacetyl]-D-thioprolyl}pyrrolidine were prepared in the same manner as in Example 25, except that (R)-(+)-1,2,3,4-tetrahydronaphthalen-2-ylacetic acid and 1-D-thioprolylpyrrolidine hydrochloride were used instead of 3-(indan-2-yl)propionic acid and 1-L-thioprolylpyrrolidine hydrochloride, respectively (yield: 59%).

mp 121°–123° C.

$[\alpha]_D$ +149.9° (c=0.72, MeOH)

IR(KBr) cm$^{-1}$: 2825–3050, 1630, 1445, 1410, 750

NMR(CDCl$_3$) δ: 1.41–1.56(1H, m), 1.79–3.62(17H, m), 3.81–3.90(1H, m), 4.66(1H, d, J=9 Hz), 4.72(1H, d, J=9 Hz), 5.11(1H, t, J=7 Hz), 7.01–7.10(4H, m)

Example 51

Colorless crystals of 3-{3-[(S)-(−)-1,2,3,4-tetrahydronaphthalen-2-ylacetyl]-L-thioprolyl}thiazolidine were prepared in the same manner as in Example 25, except that (S)-(−)-1,2,3,4-tetrahydronaphthalen-2-ylacetic acid and 3-L-thioprolylthiazolidine hydrochloride were used instead of 3-(indan-2-yl)propionic acid and 1-L-thioprolylpyrrolidine hydrochloride, respectively (yield: 38%).

mp 119°–121° C.

$[\alpha]_D$ −128.6° (c=0.73, MeOH)

IR(KBr) cm$^{-1}$: 2825–3050, 1640, 1620, 1410, 745

NMR(CDCl$_3$) δ: 1.39–1.57(1H, m), 1.93–4.25(14H, m), 4.46–4.93(4H, m), 5.07–5.21(1H, m), 7.00–7.14(4H, m)

Example 52

Colorless crystals of 3-(3-[(R)-(+)-1,2,3,4-tetrahydronaphthalen-2-ylacetyl]-L-thioprolyl}thiazolidine were prepared in the same manner as in Example 1, except that 3-[(R)-(+)-1,2,3,4-tetrahydronaphthalen-2-ylacetyl]-L-thioproline prepared in Reference Example 34 was used instead of 3-(2-indanylacetyl)-L-thioproline (yield: 37%).

mp 152°–154° C. $[\alpha]_D$ −35.7° (c=0.23, MeOH)

IR(KBr) cm$^{-1}$: 2910, 1630, 1430, 1405, 750

NMR(CDCl$_3$) δ: 1.42–3.35(13H, m), 3.67–5.18(7H, m), 7.04–7.11(4H, m)

Preparation Example 1

| Compound of Example 2 | 50 g |
| Lactose | 315 g |
| Corn starch | 125 g |
| Crystallized cellulose | 25 g |

The above components were blended to obtain a homogeneous mixture. After the addition of 200 ml of 7.5% hydroxypropyl cellulose, the mixture was made into granule by means of an extruding granulator using a screen with a 0.5 mm diameter. The granule was rounded and dried to produce a granulous preparation. The dried granule was coated with 1.9 kg of a film-coating liquid having the following composition using a fluid-type granulator to produce enteric coated granule.

| Hydroxypropylmethyl cellulose phthalate | 5.0 wt % |
| Stearic acid | 0.25 wt % |
| Methylene chloride | 50.0 wt % |
| Ethanol | 44.75 wt % |

Preparation Example 2

| Compound of Example 18 | 20 g |
| Lactose | 100 g |
| Corn starch | 36 g |
| Crystallized cellulose | 30 g |
| Calcium carboxymethyl cellulose | 10 g |
| Magnesium stearate | 4 g |

The above components were homogeneously mixed and prepared into tablets each weighing 200 mg by means of a one-shot tablet machine using a 7.5 mm screw. Spray coating was applied to the tablets to prepare enteric film-coated tablets having the film weight of 10 mg per tablet. The composition of the coating liquid was as follows:

| Hydroxypropylmethyl cellulose phthalate | 8.0 wt % |
| Glycerol fatty acid ester | 0.4 wt % |
| Methylene chloride | 50.0 wt % |
| Breached beeswax | 0.1 wt % |
| Isopropanol | 41.5 wt % |

As illustrated above, the compounds of this invention exhibit both memory improving effects and cerebral circulation/metabolism improving effects because of their prolyl endopeptidase inhibitory activity, anti-hypoxic activity, and anti-amnesic activity. In addition, the compounds have a high degree of safety. Thus they are useful as medicines for treating or preventing cerebral hemorrhage sequela, cerebral infarction sequela, cerebral arterioscleosis, subarachnoid hemorrhage sequela, cranial injury sequela, cerebral operation sequela,ration sequela, cerebrovascular dementia, Parkinson's disease, Alzheimer's disease, Pick's disease, various anoxia toxicosis including, but not limited to anthracemia sequela, cerebral alcoholoism related diseases, and the like.

What is claimed is

1. A condensed benzene derivative represented by the following (I),

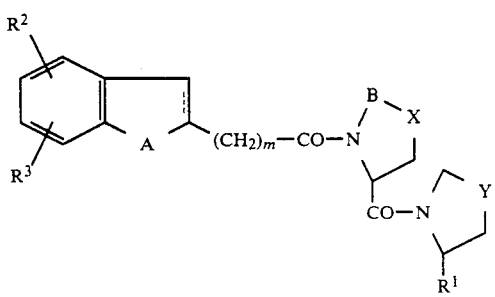

wherein A represents a methylene, ethylene, or propylene group, B represents a methylene or ethylene group, m denotes an integer of 0–5, X and Y, which may be same or different, individually represent a methylene group or a sulfur atom, $R^1$ represents a hydrogen atom, a carboxyl, lower alkyloxycarbonyl, hydroxymethyl, or formyl group, $R^2$ represents a hydrogen atom, a halogen atom, a lower alkyl, lower alkoxy, nitro, or amino group, $R^3$ represents a hydrogen atom or a lower alkyl group, and the dotted line may optionally be present.

2. A condensed benzene derivative of claim 1, which is an optical isomer or a mixture of optical isomers.

3. A condensed benzene derivative of claim 1, which is a stereoisomer or a mixture of stereoisomers.

4. A pharmaceutical composition for treating or preventing cerebral circulation disorder, cerebral metabolism disorder, or memory disturbance comprising an effective amount of the condensed benzene derivative of claim 1, 2 or 3, in admixture with a pharmaceutically acceptable carrier.

5. A method for treating or preventing cerebral circulation disorder, cerebral metabolism disorder, or memory disturbance in a subject in need thereof, which comprises administering to said subject an effective amount of the condensed benzene derivative of claim 1, 2 or 3.

* * * * *